United States Patent [19]

Saito et al.

[11] Patent Number: 5,198,192

[45] Date of Patent: * Mar. 30, 1993

[54] APPARATUS FOR DETECTING INGREDIENT IN URINE, A TOILET STOOL EQUIPPED WITH A URINE DETECTING DEVICE AND A ROOM FOR URINE DETECTING FACILITY

[75] Inventors: Shiro Saito; Ryuichi Kawamoto; Mineharu Kondo; Shigeru Sakakibara, all of Tokoname, Japan

[73] Assignee: Inax Corporation, Tokoname, Japan

[*] Notice: The portion of the term of this patent subsequent to Jan. 8, 2008 has been disclaimed.

[21] Appl. No.: 359,168

[22] Filed: May 31, 1989

Related U.S. Application Data

[63] Continuation-in-part of Ser. No. 195,557, May 18, 1988, Pat. No. 4,982,741.

[30] Foreign Application Priority Data

| Jun. 9, 1988 | [JP] | Japan | 63-75801[U] |
| Jun. 9, 1988 | [JP] | Japan | 63-75802[U] |
| Jun. 9, 1988 | [JP] | Japan | 63-75803[U] |
| Jun. 9, 1988 | [JP] | Japan | 63-75804[U] |
| Jun. 9, 1988 | [JP] | Japan | 63-75805[U] |
| Jun. 9, 1988 | [JP] | Japan | 63-75806[U] |
| Jun. 9, 1988 | [JP] | Japan | 63-75807[U] |
| Jun. 9, 1988 | [JP] | Japan | 63-75808[U] |
| Jun. 9, 1988 | [JP] | Japan | 63-75809[U] |
| Jun. 9, 1988 | [JP] | Japan | 63-75810[U] |
| Jun. 9, 1988 | [JP] | Japan | 63-75811[U] |

[51] Int. Cl.$^5$ .................. A61B 5/00; G01N 21/00; E03D 1/00

[52] U.S. Cl. .................. 422/68.1; 422/81; 422/82.01; 422/82.03; 422/82.04; 128/760; 128/771; 4/314; 4/661

[58] Field of Search .................. 422/68.1, 63, 79, 81, 422/82.01, 82.02, 82.03, 82.04, 50; 128/760, 771; 4/301, 314, 661, 420

[56] References Cited

U.S. PATENT DOCUMENTS

| 4,086,061 | 4/1978 | Hoffa et al. | 422/50 |
| 4,253,845 | 3/1981 | Smernoff | 422/50 |
| 4,636,474 | 1/1987 | Ogura et al. | 4/661 |
| 4,860,767 | 8/1989 | Maekawa | 128/760 |
| 4,901,736 | 2/1990 | Huang | 128/771 |
| 4,943,416 | 7/1990 | Kikuchi et al. | 422/63 |
| 4,961,431 | 10/1990 | Ikenaga et al. | 128/760 |
| 4,982,741 | 1/1991 | Saito et al. | 128/771 |

FOREIGN PATENT DOCUMENTS

| 292311 | 11/1985 | European Pat. Off. . |
| 0117153 | 6/1985 | Japan | 422/68.1 |
| 60-117157 | 6/1985 | Japan . |
| 60-233551 | 11/1985 | Japan . |

*Primary Examiner*—Robert J. Warden
*Assistant Examiner*—T. A. Trembley
*Attorney, Agent, or Firm*—Kanesaka & Takeuchi

[57] ABSTRACT

A urine detection device is disposed to a urine receiving surface of a toilet stool in which urine, diluting water and reagent are mixed by vertically moving a piston in the cylinder of the detection device, the reaction between them is detected by an electrode and the ingredient in urine is detected. Liquid in the cylinder is stirred by a stirring device to blown air into the reagent reservoir, by which oxygen is dissolved in the reagent. Cleaning liquid is sprayed from the nozzle to the electrode for flushing. An opening is disposed to a supporting wall of the toilet stool, through which the cylinder is detached or attached. The electrode is disposed such that its rear end is directed to the opening and detached or attached through the opening.

19 Claims, 22 Drawing Sheets

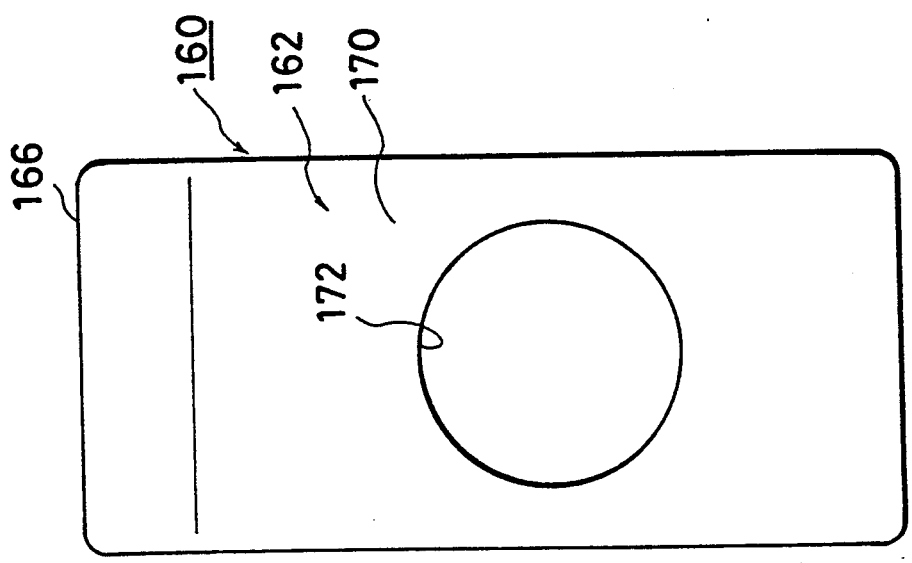
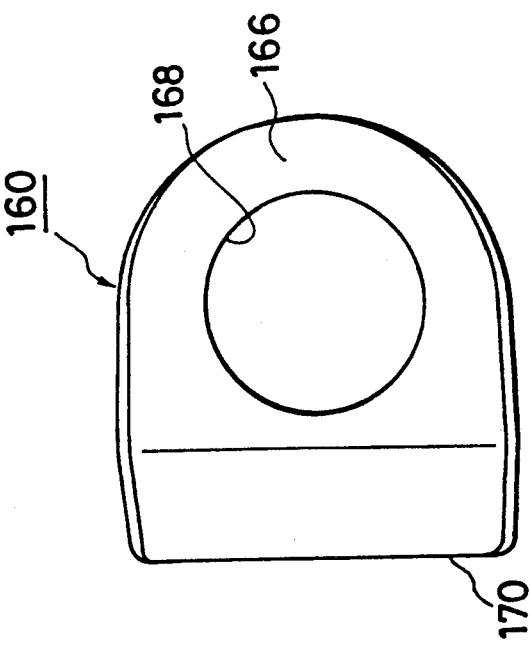

APPARATUS FOR DETECTING INGREDIENT IN URINE, A TOILET STOOL EQUIPPED WITH A URINE DETECTING DEVICE AND A ROOM FOR URINE DETECTING FACILITY

This is a continuation in part application of Ser. No. 195,557 filed on May 18, 1988, now Pat. No. 4,982,741.

FIELD OF THE INVENTION AND RELATED ART STATEMENT

The present invention concerns an apparatus for detecting an ingredient in urine, a toilet stool equipped with a urine detecting device and a system for urine detecting facility for detecting the concentration of ingredients in urine such as glucose and bilirubin, thereby enabling to judge the condition of health.

Heretofore, diabetis mellitus, etc. have been judged by detecting the concentration of glucose in urine and the function of the kidney has also been judged by detecting the concentration of bilirubin in urine. These examinations are usually made by collecting urine of a person to be examined in a beaker and serving the urine in the beaker to detection equipments, which requires detecting by specialists such as doctors or detection engineers.

Recently, it has been proposed a toilet stool having a testing portion containing a reagent at the inside thereof, in which urine discharged to the testing portion and the reagent in the testing portion are brought into reaction, so that the presence of sugar, etc. in urine can be examined depending on the change of color in the testing portion.

In such a toilet stool, glucose, etc. in urine are merely examined by the change of color but the concentration of glucose, etc. can not be determined accurately. In addition, it is not always possible to expect the proper reaction of the reagent and the urine, nor a testing portion receives a sufficient supply of the reagent, failing to provide a complete judgement of the function. Furthermore, since a great amount of discharged urine is directly mixed with the reagent for reaction, the effect of the reagent is insufficient to sometimes cause a wrong change of color. In addition, since the function of completely cleaning a the reagent and the urine after the reaction is finished, it involves a problem that no accurate function can be obtained and reliability is poor.

OBJECT AND SUMMARY OF THE INVENTION

The object of the present invention is to provide an apparatus capable of automatically and accurately detecting a ingredient in urine, as well as a toilet stool equipped with such an apparatus.

Another object of the present invention is to provide a urine detection apparatus capable of rapidly mixing urine and reagent in a cylinder and, therefore, capable of rapidly and accurately measuring the glucose concentration in urine, as well as a toilet stool equipped with such an apparatus.

Another object of the present invention is to provide a toilet stool equipped with a urine detection device capable of easily replacing reagent reservoirs.

A further object of the present invention is to provide a toilet stool equipped with a urine detection device including a waterproof system for electric circuits.

A still further object of the present invention is to provide a toilet stool equipped with a urine detection device capable of easily attaching or detaching the urine detection device or capable of easily conducting inspection, etc., as well as a toilet stool equipped with a urine detection device capable of preventing water fallen from the outer circumferential surface of the toilet stool from entering the inside of a toilet stool such as to the lower side of a bowl.

A still further object of the present invention is to provide a toilet stool equipped with a urine detection device capable of easily attaching and detaching an electrode disposed to the cylinder of the urine detection device.

A still further object of the present invention is to provide a toilet stool equipped with a urine detection device capable of calibrating an electrode detection value by using a standard solution.

A still further object of the present invention is to provide a system for urine detection facility capable of easily administrating the residue of a reagent in a reagent reservoir.

The present invention provides an apparatus for detecting an ingredient in urine comprising:

a cylinder which is disposed vertically along the axial direction thereof, so that its upper end opening defines an inlet for urine, the cylinder including a diametrically enlarged upper portion having an inside diameter which is larger than that of its other portions;

a piston fitted in the cylinder, a driving device for vertically moving the piston in the cylinder, an electrode extending through a wall portion of the cylinder which defines the diametrically enlarged portion, and having a top end position in contact with a liquid in the cylinder for detecting the concentration of an ingredient of a liquid in the cylinder, a reagent supplying device having an opening extending through the upper portion of the cylinder wall, a reagent reservoir connected through a pipeline and a pump to the opening and a valve disposed to the pipeline, so that a reagent may be supplied into the cylinder when the valve is opened; and a water supplying device including an opening extending through the upper portion of the cylinder wall, a source of water supply connected through a pipeline to the opening and a valve disposed in the pipeline, so that water may be supplied into the cylinder when the valve is opened.

In a preferred embodiment of the present invention, the reagent is an enzyme reagent capable of reacting with an ingredient in urine, and the electrode is such an electrode capable of externally outputting the state of reaction between the enzyme reagent and the urine ingredient as an electric signal.

The reagent preferably comprises an enzyme for oxidizing sugar in urine as the main ingredient.

The enzyme reagent is preferably such a reagent comprising an enzyme for oxidizing protein in urine as the main ingredient.

The electrode is preferably an oxygen electrode capable of externally outputting the amount of oxygen consumed in the oxidizing reaction between the enzyme reagent and the urine ingredient as an electric current value.

In one embodiment of the invention, a flushing nozzle may be disposed to the cylinder, so that water jetted out therefrom is spread to the top end of the electrode.

The flushing nozzle is connected by way of a pipeline and a valve to a city water pipeline and disposed such that water is jetted out from the nozzle by the water pressure in the city water pipeline.

Since water jetted out from the flushing nozzle is directly spread to the top end of the electrode, the top end of the electrode can be cleaned. Accordingly, accuracy for the detection value from the electrode becomes high.

Further, in the present invention, a stirring device for stirring liquid in the cylinder may be disposed.

Further, air may be blown into the reagent reservoir to be dissolved into the reagent in the present invention.

In the present invention, a calculator for calculating the electrode detection value and a display for indicating the result of the calculation may be disposed.

Basically, the apparatus is operated as described below.

(1) At first, the piston is lowered to the lowermost position, so that urine can be received in the cylinder.

(2) Then, the piston is raised to the uppermost position, so that urine remains only between the inner circumferential surface of the diametrically enlarged portion of the cylinder and the outer circumferential surface of the piston.

(3) Predetermined amounts of water and reagent are supplied into the cylinder while lowering the piston to its lowermost position.

(4) The state of reaction between urine and reagent is detected by the electrode. That is, concentration of an ingredient in urine is detected based on a detection signal from the electrode.

(5) Electrode signal is processed in the calculator, to calculate the ingredient in urine and the results are indicated on the display.

In the case of using glucose oxidase as the enzyme reagent, glucose in urine is detected by the procedures as described below.

When glucose oxidase and urine are mixed, if glucose is contained in urine, glucose oxidizing reaction occurs. The oxidizing reaction proceeds more rapidly as the glucose concentration in urine becomes higher. Further, along with the reaction, oxygen in the reaction solution (a mixed solution of examined urine diluted as necessary and glucose oxidase) is consumed, by, by which the oxygen concentration in the reaction solution is lowered. Accordingly, it is possible to detect the change of the oxygen concentration in the reaction solution based on the change of the detection value from the electrode to detect the glucose concentration.

Referring more specifically, as shown in FIG. 9, the current value from the oxygen electrode is reduced more rapidly, after mixing glucose oxidase and urine, as the concentration of glucose in urine is higher.

Accordingly, concentration of glucose in urine can be detected by determining average variation coefficient ($\Delta A/\Delta t$) for the current value in a period of time in which the current value is continuously reduced as seen between points (b) and (c). The relationship between the average variation coefficient and the glucose concentration can previously be determined by a test using a standard solution and the concentration of glucose in urine can be determined based on the detected average variation coefficient by using the above-mentioned relationship as a calibration curve or inputting the same to the calculator.

Since the reaction rate of glucose also changes depending on temperature, the glucose concentration is calibrated in accordance with the temperature of the reaction solution.

In the present invention, since the device for stirring the liquid in the cylinder is disposed, urine and reagent or diluting water can be mixed rapidly and sufficiently, thereby enabling highly accurate urine detection.

In the present invention, water for flushing a cistern containing a sufficient amount of oxygen is suitably used in diluting water for urine. That is, water in the cistern is discharged and sprayed from a ball tap to the inside of the cistern to sufficiently in contact with air upon discharge (since water drops as minute droplets, area of contact between water and air is remarkably large). Accordingly, the concentration of dissolved oxygen in water of the cistern is substantially or nearly saturated and glucose can be oxidized efficiently by using such water as the diluting water. By the way, if the amount of dissolved oxygen is less, reaction with glucose is retarded by so much or, if the concentration of glucose in the examined urine is extremely high, no sufficient oxidization is conducted to glucose, which may possibly reduce the detected value than a true level. In the present invention, glucosuria can be detected at high accuracy irrespective of the concentration of glucose in the examined urine.

By blowing air into the reagent in the reagent reservoir, oxygen is dissolved up to a substantially or nearly saturated level in the reagent. Accordingly, glucose oxidizing reaction can proceed surely and efficiently, thereby enabling detection for glucosuria at high accuracy. In a preferred embodiment of the present invention, the reagent reservoir is disposed remote from the toilet stool. Since the reagent reservoir is isolated from the toilet stool in this way, the reagent reservoir can be replaced easily. Further, adherance of deposited scales, etc. on the toilet stool to hands can be prevented upon replacement of the reservoirs.

Furthermore, in another embodiment of the present invention, a control box is disposed separately from the toilet stool. In this constitution, water at the periphery of the toilet stool is not spread to the electric circuit to provide protection therefor.

The present invention, in another aspect, provides an apparatus for detecting an ingredient in urine comprising:

a toilet stool having a bowl, a through hole formed to the urine receiving surface of the bowl, a supporting wall portion surrounding the outer surface of the bowl and supporting the bowl to the floor surface, an opening formed to the supporting wall portion, a closure member for closing the opening and a suspending portion formed above the opening and covering the upper outer surface of the closure member and a urine detection device secured to the bowl so that urine enters from the through hole.

In this toilet stool equipped with the urine detection device, urine discharged to the bowl is introduced into the urine detection device, diluted with water, if required, and a reagent is added thereto for measuring the ingredient in urine by the electrode.

An opening is disposed on the side or at the front of the supporting wall portion of the toilet stool, through which the urine detection device can be attached, detached or inspected. The closure member is mounted to the opening and the suspending portion is disposed above the opening so as to cover the upper portion of the closure member, by which water falling along the outer circumferential surface of the toilet stool falls from the suspending portion and does not enter the inside of the toilet stool, that is, to the inside of the supporting wall portion. This can keep from getting musty at the inside of the toilet stool.

A further embodiment of the present invention comprises:

a toilet stool having a bowl, a through hole formed to the urine receiving surface of the bowl, a supporting wall portion surrounding the outer surface of the bowl and supporting the bowl to the floor surface, an opening formed to the supporting wall portion and a closure member for closing the opening; and a urine detection device to which urine enters from the through hole, in which the opening formed to the supporting wall portion has such a side as allowing the urine detection device to pass therethrough. In this apparatus, the detection device can be attached or detached through the opening formed to the supporting wall portion.

In a further embodiment of the present invention, the upper end of the cylinder is connected to a cylinder mounting port opened to the bowl at the inside of the supporting wall portion. Further, an opening attached with a closing cover having such a size as allowing the cylinder to pass therethrough is disposed at the front or on the side of the supporting wall portion, and the cylinder is attached to the bowl so that the electrode is situated on the side of the opening.

The electrode of the urine detection device can be operated by inserting a hand through the opening disposed to the supporting wall portion. Since the electrode is disposed so that it is situated on the side of the opening relative to the cylinder, the operation can be conducted easily.

In a still further embodiment of the present invention, a sleeve is inserted through the through-hole in the urine receiving surface of the bowl and secured to the toilet stool, and the cylinder is screwed to the lower end of the sleeve.

In a still further embodiment of the present invention, the driving device is attached to the cylinder and, when the cylinder is rotated for screwing the cylinder into the sleeve, the driving device is also rotated together with the cylinder.

The driving device may be a linear actuator.

In a still further embodiment, a flushing cistern is disposed to the toilet stool and water in the cistern is supplied into the cylinder.

In this case, a recessed groove extended vertically is formed at the rear face of the cistern and a pipeline for introducing water from the cistern to the cylinder can be disposed in the recessed groove. With such a constitution, since the recessed groove is formed at the rear face of the cistern and the pipeline for urine detection device is disposed in the recessed groove, the toilet stool can be disposed such that the rear face of the cistern is in close contact with the wall surface.

The present invention provides a further embodiment of the apparatus for detecting an ingredient in urine, comprising:

a toilet stool, a cylinder capable of receiving urine from the through-hole disposed to the urine receiving surface of a bowl in the toilet stool;

a reagent supplying device for adding a reagent to urine introduced into the cylinder, an electrode to be in contact with urine to which the reagent is added, for detecting the ingredient in urine and a standard solution supplying device for supplying a standard solution for the calibration of the electrode in the cylinder.

With such a constitution, the standard solution is introduced, as required, into the urine detection device to calibrate the detection value of the electrode.

When the electrode outputs are compared between an electrode which is newly attached or cleaned efficiently with no deposition of contaminates at all and an electrode deposited with contaminates, each being in contact with a liquid of an identical ingredient concentration, the output value of the electrode deposited with the contaminates is generally lower than the output value of the electrode newly attached or sufficiently cleaned. In the same manner, in a case where a plurality of newly attached electrodes are brought into contact each with a liquid of an identical ingredient concentration, the output value may sometime different depending on every electrodes.

With respect to the individual difference between the electrodes, in the constitution as described above, a standard solution is introduced into the urine detection device to examine the output value of the electrode in the urine detection device. Then, the detected value is compared with a standard output value to compensate the detection value. A specific example is to be explained referring to FIG. 22. In a case where an electrode shows normal output operation, the ingredient concentration in urine and the electrode output value has a relationship as shown by a reference calibration line A in FIG. 22. In this case, when the electrode is brought into contact with the standard solution, it outputs a standard output value b.

As contaminates are deposited to the electrode, the output value when the electrode is brought into contact with the standard solution is reduced to b'. In this case, the urine ingredient is determined from the electrode output value by using a calibration line represented by A'. In this way, concentration of the ingredient in urine can be detected extremely accurately even if there is any individual difference between electrodes or contaminates are deposited to the electrode.

As the standard solution, an aqueous solution at a predetermined concentration of a compound for measuring an ingredient in urine, e.g., glucose or bilirubin is used.

In the present invention, the standard solution can automatically be supplied from the reagent reservoir to the urine detection device. It may be considered to transfer the standard solution, for example, to a beaker which is then poured manually into the urine detection device. However, the calibration procedures are made simple and convenient by constituting such that the reagent is automatically supplied as described above.

The present invention further provides a system for urine detection facility comprising:

a plurality of chambers, a toilet stool disposed to each of the chambers, a urine detection device disposed to each of the toilet stools so as to receive urine, and a reagent supplying device including a reagent reservoir for supplying a reagent for detecting an ingredient in urine to each of the urine detection devices, in which the urine detection device has an electrode for detecting the ingredient in urine, and the reagent is supplied to each of the urine detection devices from a common reagent reservoir.

In this system for urine detection facility, when a person to be examined enters one chamber and discharges urine into the toilet stool, the urine is introduced into the urine detection device. Then, the reagent is added to the urine and the urine ingredient is detection by the electrode.

In the system, since the reagent is supplied to each of the urine detection device from a common reagent reservoir, reagent residue control or exchange of the reagent reservoir may be conducted only to the common reagent reservoir.

Since the room for urine detection facility has a plurality of toilet stools each equipped with the urine detection device, it is suitable to be used in hospitals, etc.

BRIEF DESCRIPTION OF THE DRAWINGS

FIG. 11 is a top plan view for the closure member;

FIG. 12 is a rear elevational view thereof;

DETAILED DESCRIPTION OF PREFERRED EMBODIMENTS

Figure 1:
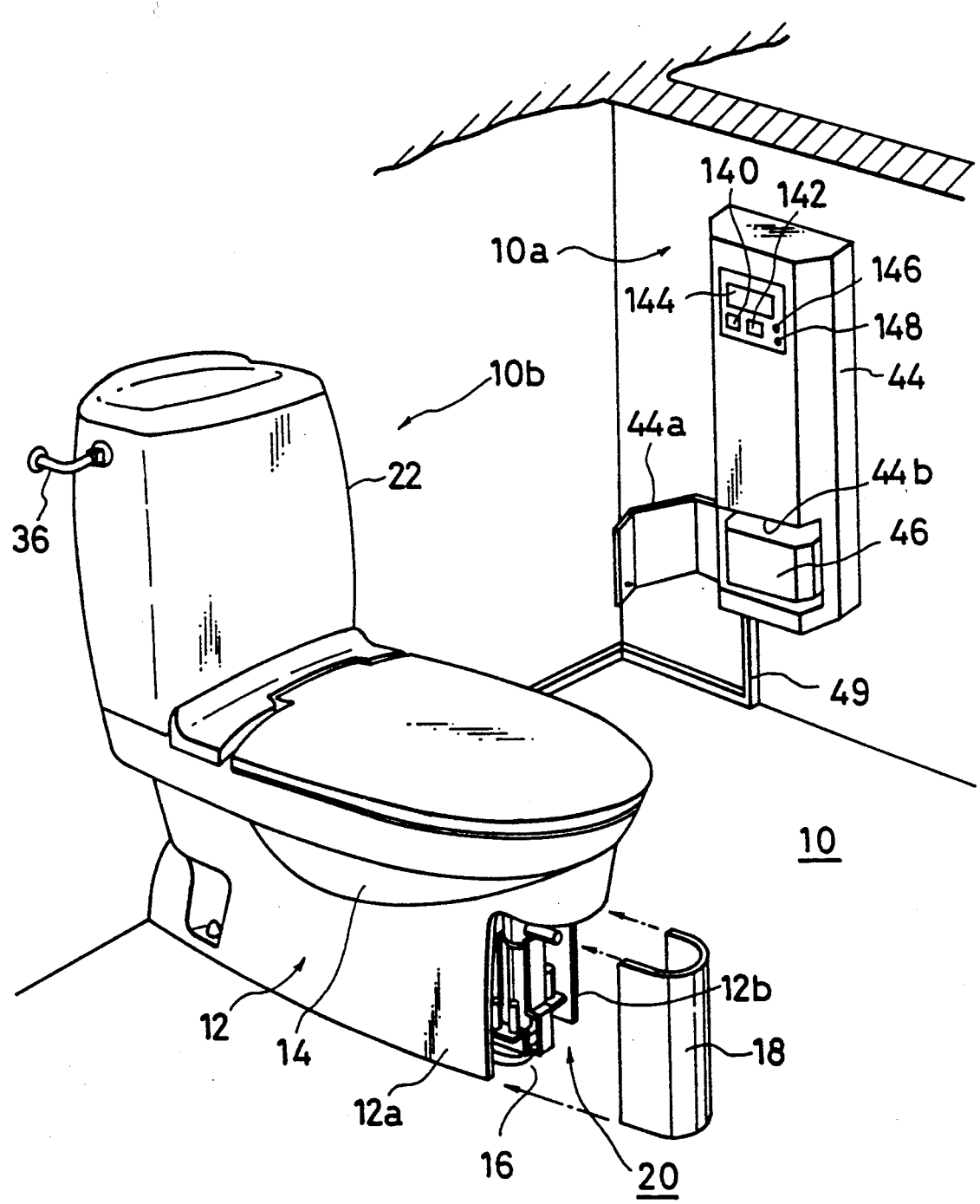
FIG. 1 is a perspective view of a toilet stool according to one embodiment of the present invention.

The present invention is to be explained by way of preferred embodiments referring to the drawings.

Figure 2:
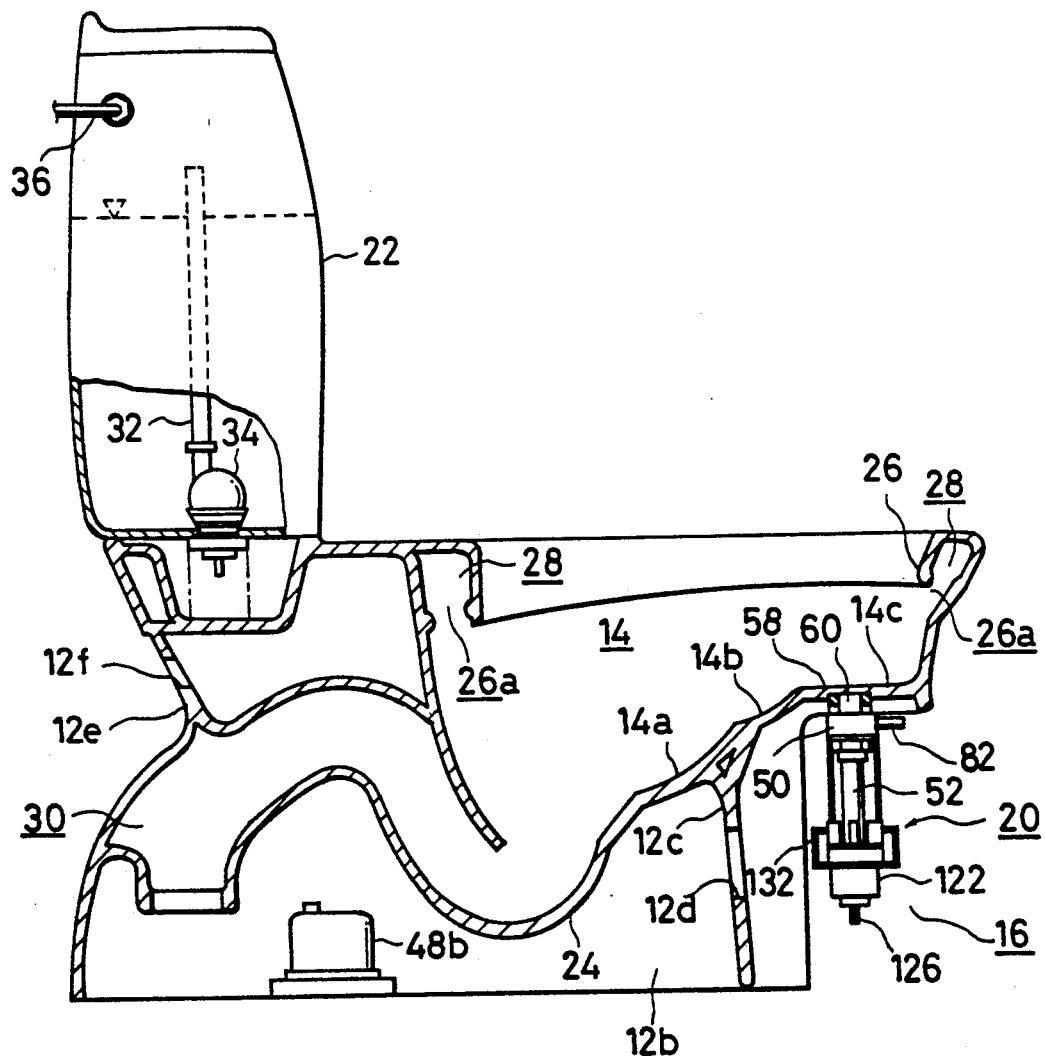
FIG. 2 is a cross sectional view thereof.

FIG. 1 is a perspective view of a toilet stool equipped with a urine detection device in one embodiment according to the present invention; FIG. 2 shows a side elevational view of the toilet stool and FIG. 3 is a top plan view of the toilet stool, in which a stool sheet and a stool cover are not illustrated in FIGS. 2 and 3.

Figure 3:
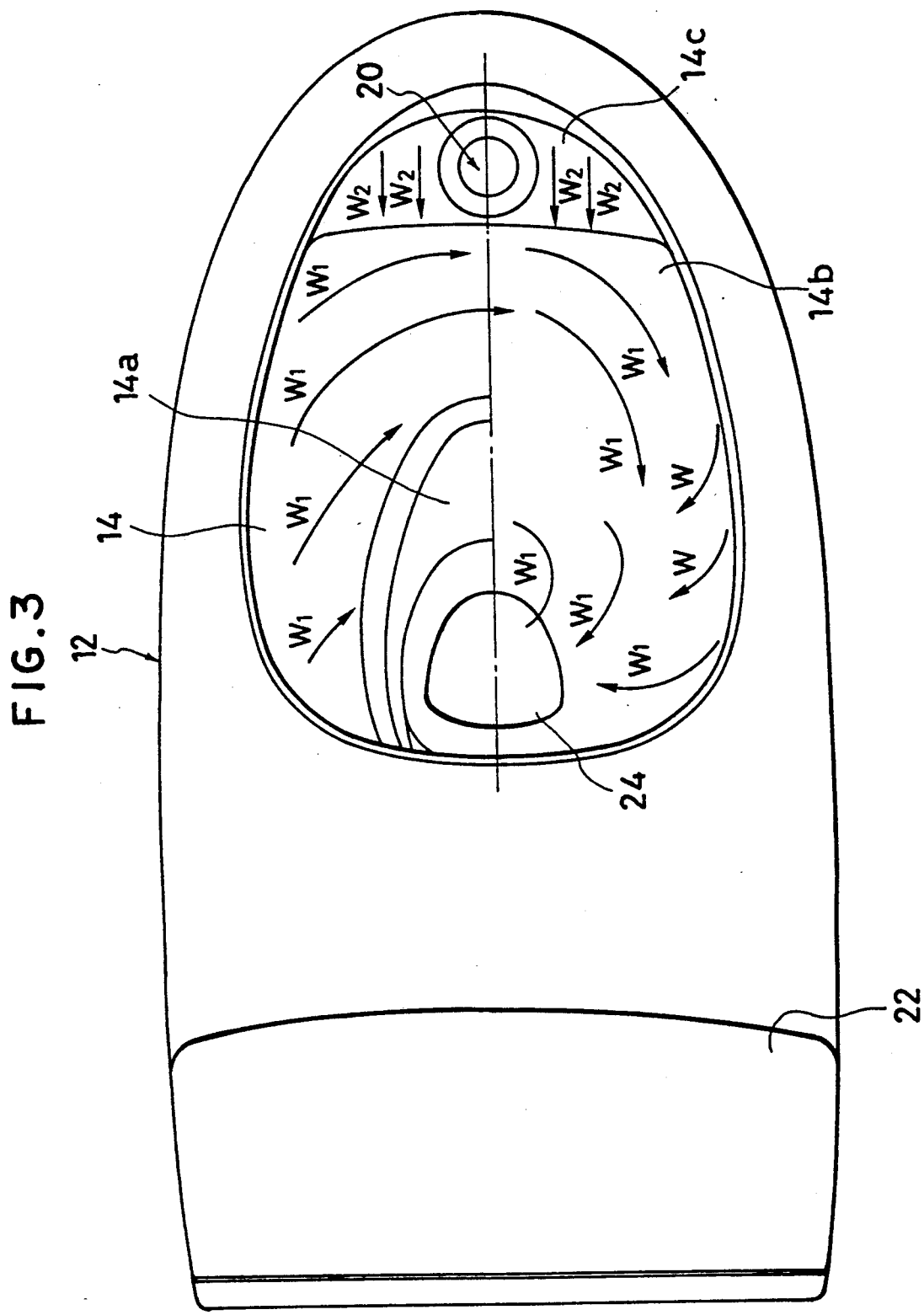
FIG. 3 is a top plan view thereof.

In FIGS. 1-3, a toilet stool 12 is disposed in a toilet room 10. A bowl 14 is formed in the front part of the toilet stool 12. In the lower region of the bowl 14, side portions 12a, 12b of the toilet stool 12 are disposed integrally so as to surround the lower region. The side portions 12a and 12b also have a function of supporting the bowl 14 to the floor surface, thereby constituting a supporting wall portion.

An opening 16 is formed at the front portion of the side portions 12a and 12b by recessing the supporting wall portion from below and a cover 18 constituting a closure member 160 described later is disposed to the opening 16. A urine detection device 20 is disposed in the lower region of the bowl 14 surrounded by the side portions 12a and 12b. The opening 16 has such a size as allowing the urine detection device 20 therethrough. Detailed structure of the urine detection device 20 to pass is described later.

At the back of the urine detection device 20, a skirt portion 12c is disposed so as to suspend from the bowl 14 and the skirt portion 12c is in contiguous with left and right side portions 12a and 12b.

A perforation 12d is formed to the skirt portion 12c for leading out pipelines $L_1$, $L_3$, $L_7$, $L_8$ and electric wirings (not illustrated) described later. A perforation 12f is also disposed to the rear portion 12e of the toilet stool 12 for leading out pipelines $L_1$, $l_3$, $L_7$, $L_8$, electric wirings and an air pipeline 48c described later. A flushing cistern 22 capable of storing flushing water is disposed to the upper rear surface of the toilet stool 12.

In this embodiment, as shown in FIG. 2, the bowl 14 of the toilet stool has a three-stepped shape, comprising a first bowl surface 14a curved and slanted upwardly from a trap 24 for forming a water seal, a second bowl surface 14b curved and upwardly slanted further above the first bowl surface 14a and a third bowl surface 14c formed horizontally from the second bowl surface 14b, in which the third bowl surface 14c is in contiguous with a rim 26. A water channel 28 is formed in the inner hollow portion of the rim 26. The water channel 28 is in communication with the cistern 22, so that flushing water in the cistern 22 is caused to flow into the water channel 28 and then flow down from a water flushing hole 26a formed to the lower surface of the rim 26 to the bowl 14. The trap 24 is in communication with a water drain channel 30 and wastes in the trap 24 are discharged externally through the water drain channel 30.

As shown in FIG. 2, an overflow pipe 32 is situated in the cistern 22 and a water passage is formed to the lower end of the overflow pipe 32 for communication with the water channel 28, in which a spherical ball valve 34 is disposed so as to shut-off the water passage. The ball valve 34 is opened or closed by a driving mechanism comprising a rotary solenoid (not illustrated).

Figure 8:
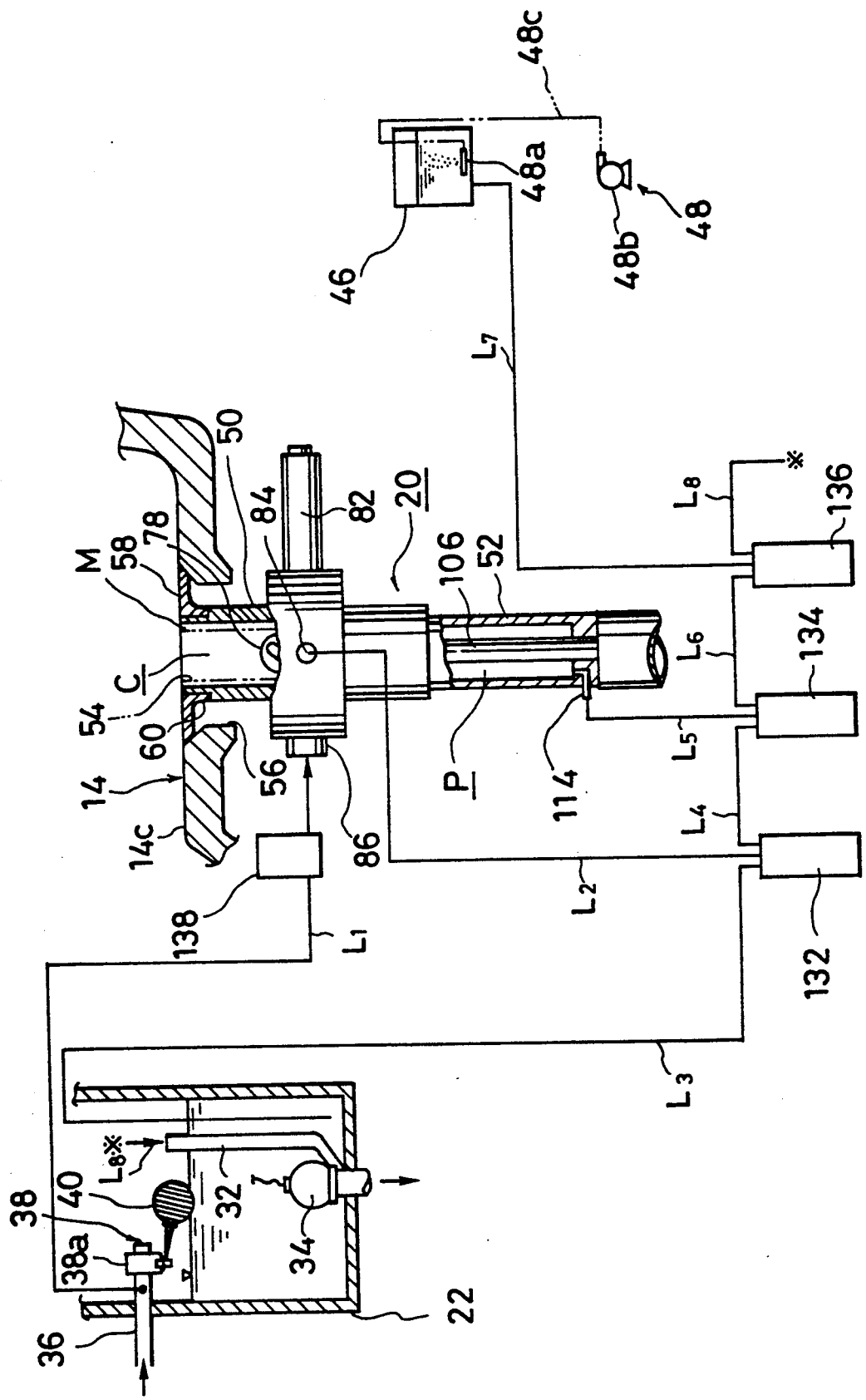
FIG. 8 is a diagram showing the pipeline system.

Further, as shown in FIG. 8, a bowl tap 38 is installed in the cistern 22 for introducing city water from an external city water pipe 36, and the bowl tap 38 has such a structure that it can be opened or closed by a float 40 disposed floatably in the cistern 22 to maintain the water level in the cistern 22. The pipeline $L_1$ is connected to the ball tap 38 at the upstream to the valve portion 38a, so that the city water may be supplied to a urine sampling cylinder described later while maintaining the water supply pressure of city water.

Most of the flushing water flowing down from the flushing hole 26a of the rim 26 at the circumferential edge of the toilet stool 12 forms swirls as shown by $W_1$ in FIG. 3 and then flows down as swirls into the trap 24 after flushing the first bowl surface 14a and the second bowl surface 14b. Flushing water $W_2$ flowing down from the flushing water hole 26a in the front portion of the rim 26 flows down along the horizontal third bowl surface 14c of the toilet stool 14 and joins the swirls $W_1$. In the usual case of using the toilet stool, upon flushing the bowl 14, swirls $W_1$ containing wastes do not flow to the upper surface of the urine detection device 20 disposed to the third bowl surface 14c.

As shown in FIG. 1, a control box 44 is disposed on the wall surface 10a of the toilet room 10. A reagent reservoir 46 is formed in the control box 44. The control box 44 has an opening 44b equipped with a door 44a for replacing the reagent reservoir 46.

In this embodiment, as shown in FIG. 8, an air blowing device 48 is disposed next to the reagent reservoir 46. The blowing device 48 has an air diffuser pipe 48a disposed in the reagent reservoir 46 and an air pump 48b, for example, a diaphragm pump. When air from the air pump 48b is blown by way of an air pipeline 48c from the air diffuser pipe 48a into the reagent, a saturated amount of oxygen is dissolved into the reagent. As shown in FIG. 2, the air pump 48b is disposed in the toilet stool 12. In FIG. 1, reference numeral 49 denotes a pipeline cover through which the air pipeline 48c and a signal cable are extended.

In this embodiment, the pipeline 48c is extended at the midway thereof to a position higher than the reagent reservoir 46 in the vertical direction (hereinafter referred to as a high level portion). Further, the air pipeline 48c is disposed with an opening (not illustrated) at or near the high level portion. By disposing the opening, among a greater amount of air sent from the air pump 48b, only a required amount of air is discharged through the opening to the outside of the pipe line 48c, to supply only an appropriate amount of air to the air diffuser pipe 48a. Further, when the operation of the air pump 48b is stopped and the pressure of the inside of the pipeline 48c tends to be negative, since atmospheric air flows through the opening into the pipeline 48c, flowing of the reagent in the reagent reservoir 46 into the air pump 48b is prevented. It is preferred that the pipeline 48c is disposed at a high level portion within the cistern 22.

Figure 4:
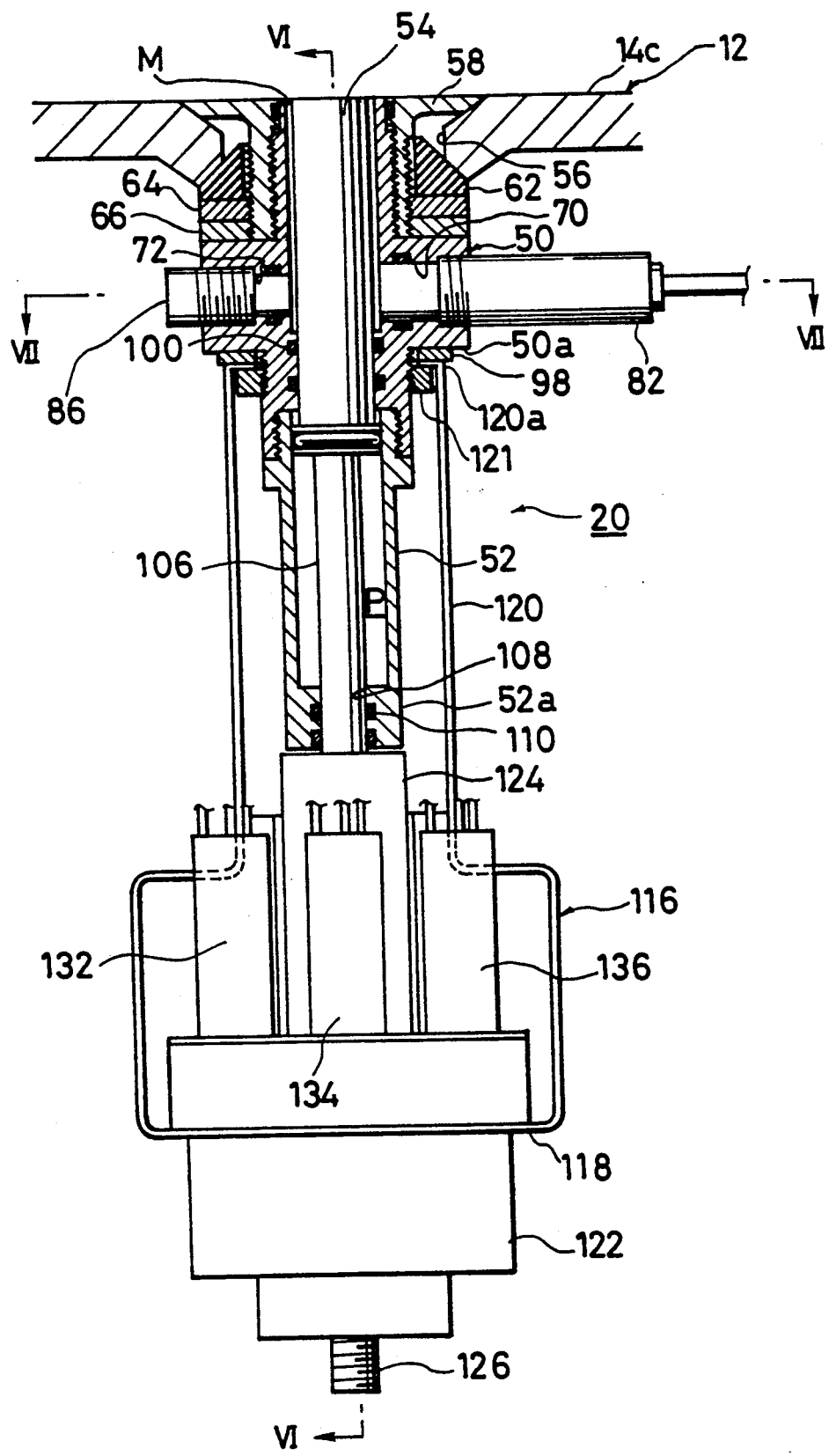
FIGS. 4, 5 and 6 are cross sectional views of a urine sampling device.
Figure 5:
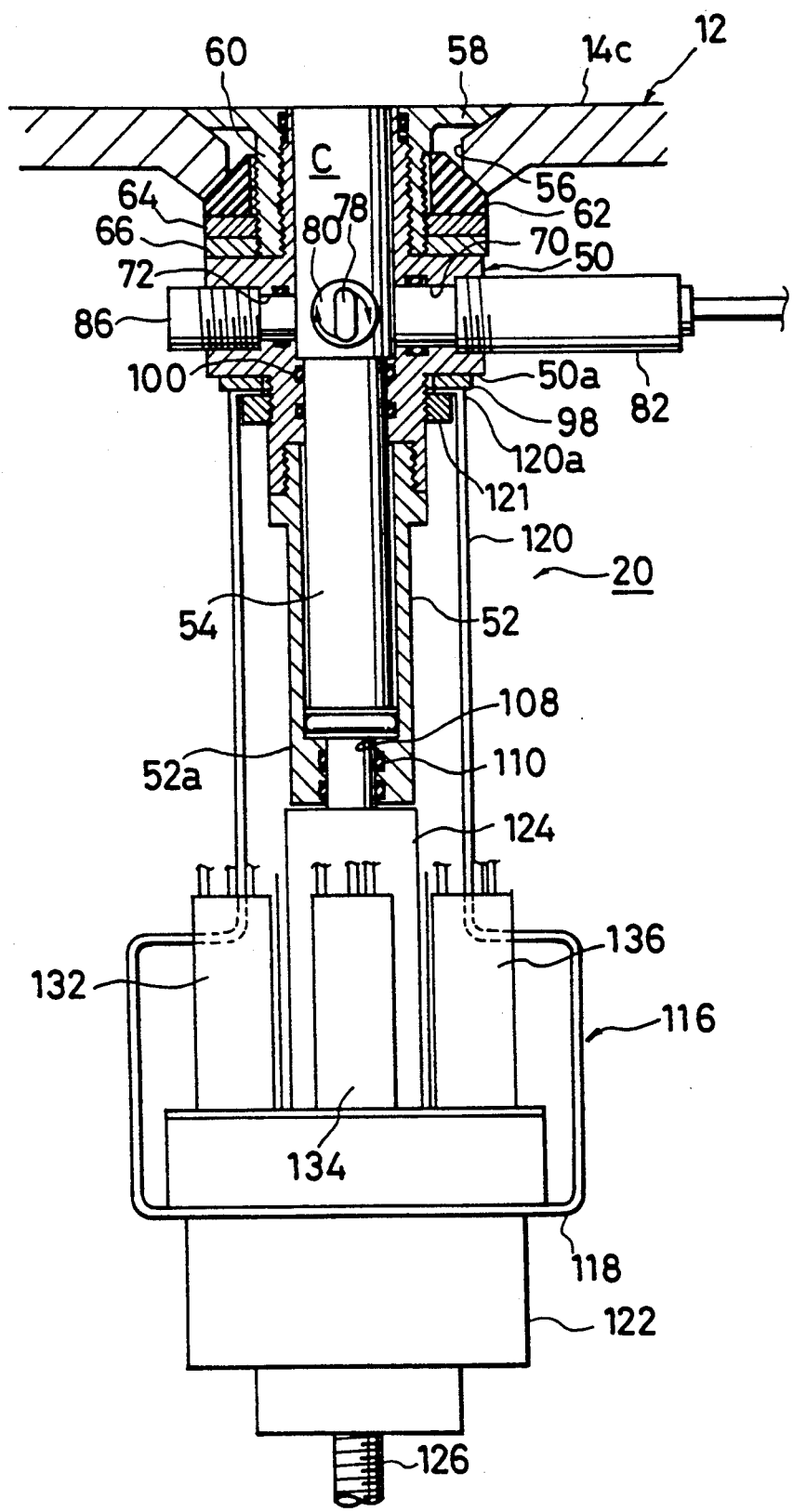
Figure 6:
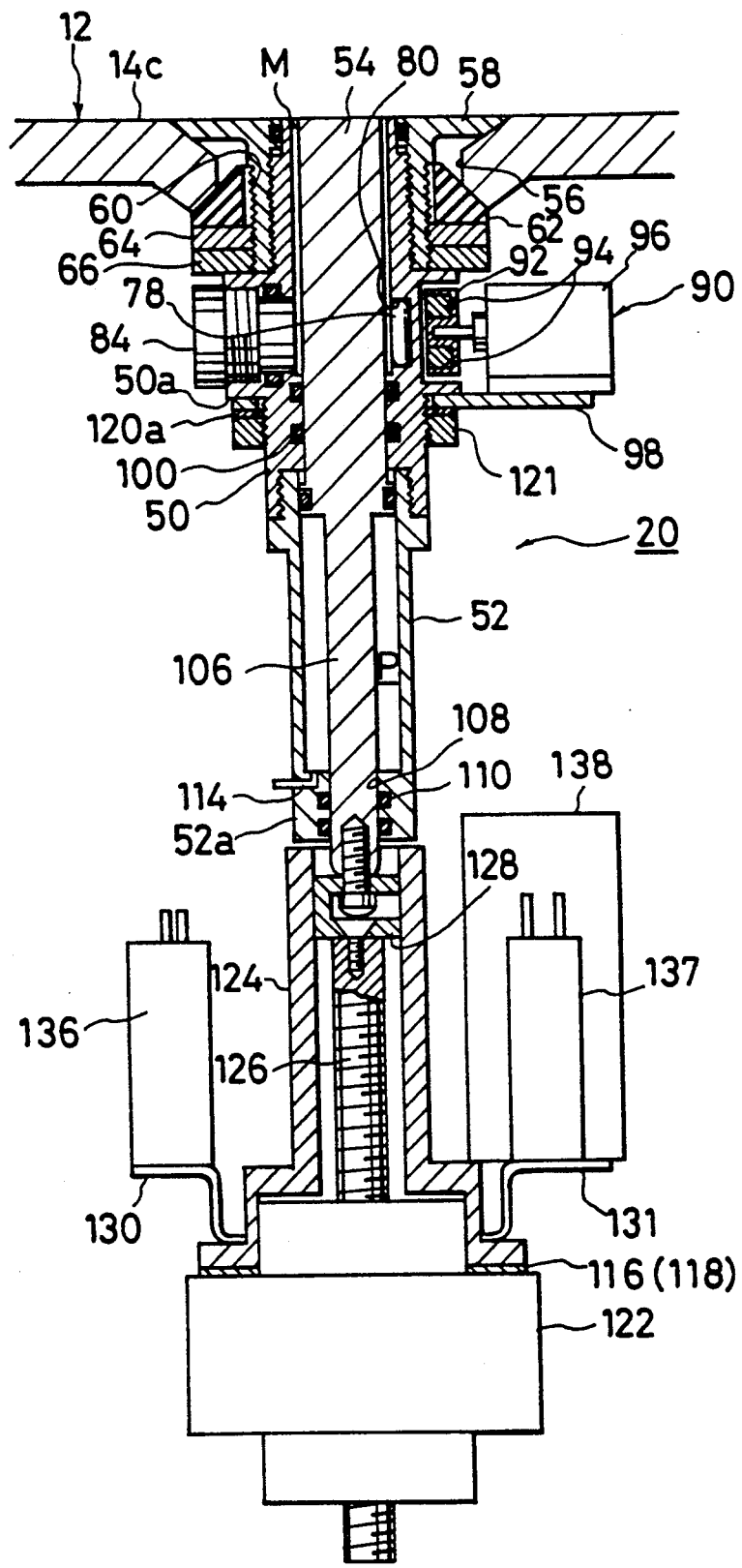
Figure 7:
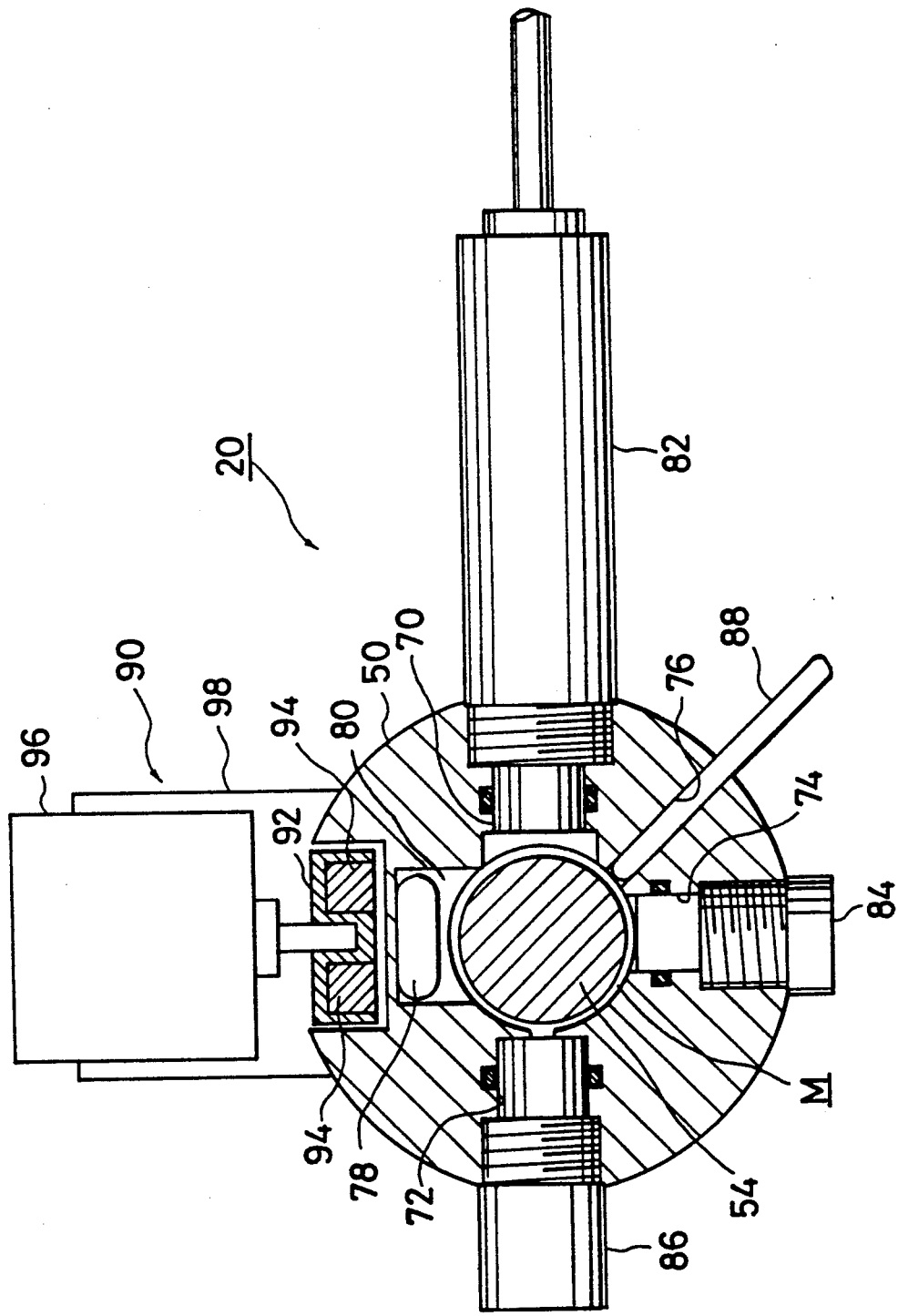
FIG. 7 is a cross sectional view take along line VII—VII in FIG. 4.

Then, the structure of the urine sampling device is to be explained referring to FIGS. 4–7. FIG. 4 is a vertical cross sectional view of the urine detection device in a state where the piston is raised, FIG. 5 is a vertical cross sectional view of the urine detection device in a state where the piston is lowered, FIG. 6 is a cross sectional view taken along line VI—VI in FIG. 4 and FIG. 7 is a cross sectional view taken along line VII—VII in FIG. 4.

The urine detection device 20 comprises a urine sampling cylinder 50, a pump cylinder 52 coaxially connected below the urine sampling cylinder 50 and a piston 54 vertically slidable in the urine sampling cylinder 50 and the pump cylinder 52. An opening 56 for attaching the urine detection device is disposed to the third bowl surface 14c of the bowl 14 and a short sleeve 60 having a flange 58 at the upper end and engraved with male threads on the side circumferential surface is inserted from above. The sleeve 60 is secured to the toilet stool 12 by tightening nuts 64 and 66 from below by way of a trigonal packing 62. The flange 58 is disposed such that the upper surface thereof is substantially flush with the upper surface of the third bowl surface 14c.

Female threads are cut along the inner circumferential surface of the sleeve 60, while male threads are cut along the upper outer circumferential surface of the urine sampling cylinder 50, so that the urine sampling cylinder 50 is coupled and secured to the sleeve 60 by screwing the male threads of the cylinder to the female threads of the sleeve 60.

The urine sampling cylinder 50 is cut with female threads at the lower inner circumferential surface thereof, while the pump cylinder 52 is cut with male threads at the upper outer circumferential surface thereof, so that the pump cylinder 52 is integrated with the urine sampling cylinder 50 by screwing the upper end of the pump cylinder 52 to the lower end of the urine sampling cylinder 50. The urine sampling cylinder 50 defines at its inside a cylindrical urine sampling chamber C (refer to FIG. 5). The urine sampling cylinder 50 has the wall surface perforated with an electrode connection port 70 in communication with the urine sampling chamber C, a flushing hole 72 perforated at a position opposing to the electrode connection port 70, a water injection hole 74 perforated at the wall surface displaced by 90° relative to the electrode port 70 and the flushing hole 72, and a thermister hole 76 respectively and, further, formed with a recess 80 for containing a stirring piece 78. An oxygen electrode 82 is screwed from the outside into the electrode connection port 70, while a water injection metal cap 84 is screwed to the water injection hole 74. Further, a cleaning nozzle 86 is screwed with the flushing hole 72 from the outside, while a rod-like thermister 88 is inserted from the outside into the thermister hole 76.

Reference numeral 90 denotes a stirring device comprising a stirring piece 78 made of a rod-like magnetic member and disposed within the recess 80, a rotational arm 92 disposed to the outside of the recess 80 opposit to the urine sampling cylinder 50 by way of a pipe wall surface, a pair of magnets 94 secured to the rotational arm 92, and a motor 96, the top end of the rotational shaft of which is secured to the rotational arm 92. The motor 96 is supported on the urine sampling cylinder 50 by way of a bracket 98.

O-rings 100 are mounted in a two step form at the inner circumference of the urine sampling cylinder 50 so as to secure a liquid tight seal between the piston 54 and the inner circumferential wall of the urine sampling cylinder 50.

The inner diameter at the upper portion of the urine sampling cylinder 50 is made greater than the inner diameter for the lower portion thereof, so that a clearance M is formed between the outer circumferential wall of the piston 54 and the upper inner circumferential wall of the urine sampling cylinder 50 when the piston 54 moves to the upper part of the urine sampling cylinder 50.

The pump cylinder 52 coaxially connected to the lower end of the urine sampling cylinder 50 defines a cylindrical pump chamber P at the inside thereof.

A rod hole 108 through which a piston rod 106 is inserted is formed to the center of a base 52a at the lower end of the pump cylinder 52, and two O-rings 110 are mounted in the rod hole 108. A conduit hole 114 is perforated through the base 52a for communicating the inside and the outside of the pump cylinder 52.

The upper end of a driving portion support frame 116 is connected to the side circumferential surface of the urine sampling cylinder 50. The supporting frame 116 comprises a horizontal portion 118 and a pair of standing portions 120 upstanding from the end of the horizontal portion. The upper end 120a of the standing portion 120 is held together with the motor supporting bracket 98 to the urine sampling cylinder 50 by means of a nut 121. That is, the urine sampling cylinder 50 has male threads cut at the lower outer circumferential surface thereof, to which the nut 121 is screwed. Then, the upper end 120a of the standing portion and the bracket 98 are put between the lower surface of the diametrically enlarged portion 50a of the urine sampling cylinder 50 and the nut 121.

A linear actuator 122 and a guide sleeve 124 are secured to the horizontal portion 118. The linear actuator 122 comprises at its inside a rotor nut (not illustrated) and a nut driving coil and constituted such that the rotor nut can be rotated accurately by a predetermined number of rotation in the same manner as usual step motors. Reference numeral 126 denotes a screw shaft meshing with the rotor nut and advanced and retracted vertically by the rotation of the rotor nut and passed through the linear actuator 122.

The upper portion of the screw shaft 126 is inserted through the guide sleeve 124 and the upper end of the screw shaft 126 is connected with a slide piece 128. The lower end of the piston rod 106 is connected with the slide piece 128, and the screw shaft 126 and the piston rod 106 are integrally moved vertically. The slide piece 128 moves slidably within the guide sleeve 124 to guide the upper end of the screw shaft 126 and the lower end of the piston rod 106.

Three electrically driven type 3-way valves 132, 134 136 and a 2-way valve 138 are disposed by way of brackets 130 and 131 to the support frame 116. FIG. 8 is a diagram showing connection of pipelines for the 3-way valves 132–138, the 2-way valve 138 with the urine sampling cylinder 50, the pump cylinder 52, the reagent reservoir 46, the ball tap 38, the cistern 22, etc.

The flushing nozzle 86 of the urine sampling cylinder 50 is connected by way of the pipeline $L_1$ to the ball tap 38 at the upstream of the valve portion and the 2-way valve 138 is disposed at the midway of the pipeline $L_1$.

Among three ports of the 3-way valve 132 the first port is connected by way of the pipeline $L_2$ to the water injection metal cap 84 of the urine sampling cylinder 50, the second port is connected by way of the pipeline $L_3$ to the inside of cistern 22 and the third port is connected by way of the pipeline $L_4$ to the first port of the 3-way valve 134.

The second port of the 3-way valve 134 is connected by way of the pipeline $L_5$ to the conduit hole 114 of the pump cylinder 52 and the third port is connected by way of the pipeline $L_6$ to the first port of the 3-way valve 136.

The second port of the 3-way valve 136 is connected by way of the pipeline $L_7$ to the reagent reservoir 46 and the third port is in communication with the inside of the bowl 14 by way of the pipeline $L_8$. The pipeline $L_8$ is led out from the rear portion of the toilet stool 12, extended upwardly along the rear face of the cistern 22 and, further, inserted into the overflow pipe 32. Water discharged from the top end of the pipeline $L_8$ flows through the inside of the overflow pipe 32 and the water passage succeeding thereto to the inside of the bowl 14. The pipeline $L_3$ is also led out from the rear portion of the toilet stool 12, extended along the rear face of the cistern 22 and then inserted into the cistern 22, the top end of which is immersed to the bottom of the cistern 22.

A detection signal from the thermister 88 is inputted by way of a signal line to a control board (not illustrated) in the control box 44. The control box has a preparatory switch 140, a detection start switch 142, a display panel 144 and display lamps 146 and 148, which are connected by way of wirings to the control board. Further, a control circuit and a calculation circuit for conducting a series of controls and calculation described later are disposed in the control board. Control signals are outputted from the control board to a driving device (not illustrated) for the 3-way valves 132–136, the 2-way valve 138 and the ball valve 134 of the cistern.

In this embodiment, glucose oxidase as an enzyme reagent is sealed in the reagent reservoir 46 for detecting glucose in urine.

As has been described above, in this embodiment, the reagent reservoir 46 is disposed in the control box 44 and, since the control box 44 is isolated from the toilet stool 12, there is no trouble for a user, for example, looking into the lower portion of the toilet stool upon replacing the reagent reservoir 46, and the reagent reservoir 46 can be exchanged easily. Further, since no access is necessary to the toilet stool 12 upon replacement, deposited matters on the toilet stool can be prevented from adhering to the user's hand.

Further in this embodiment, since the control board is disposed remote from the toilet stool, there is no worry that water relevant to the toilet stool (for example, water leaked from the bowl or cistern, water condensated to the outer surface of the bowl or cistern or water used for flushing the toilet stool) may be in contact with the control board, by which the electric circuits can be protected. In this embodiment, since the reagent reservoir 46 is disposed below the control board, if the reagent should be leaked from the reagent reservoir, it does not wet the control board.

Figure 10:
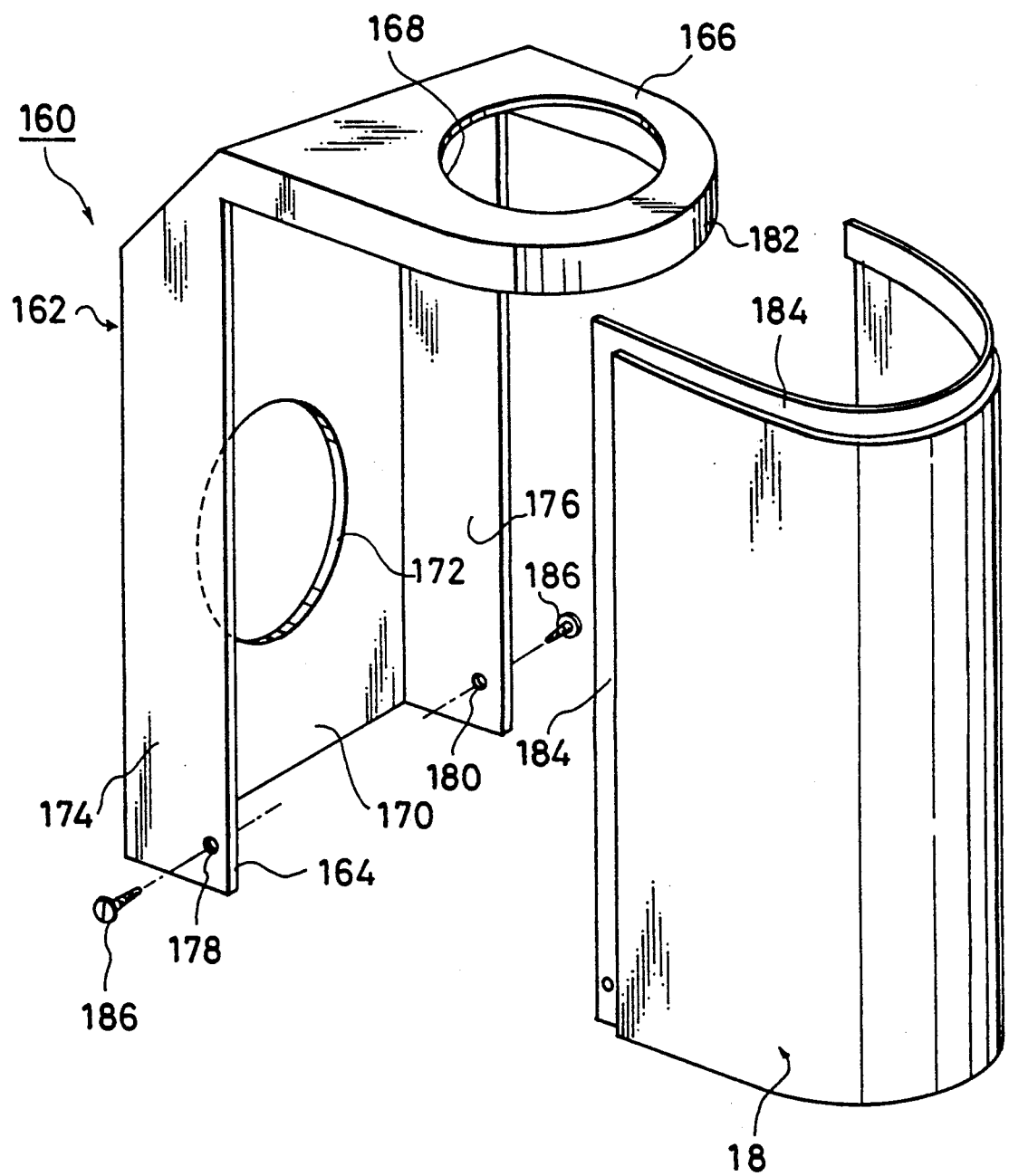
FIG. 10 is a view illustrating the assembling of a closure member.
Figure 13:
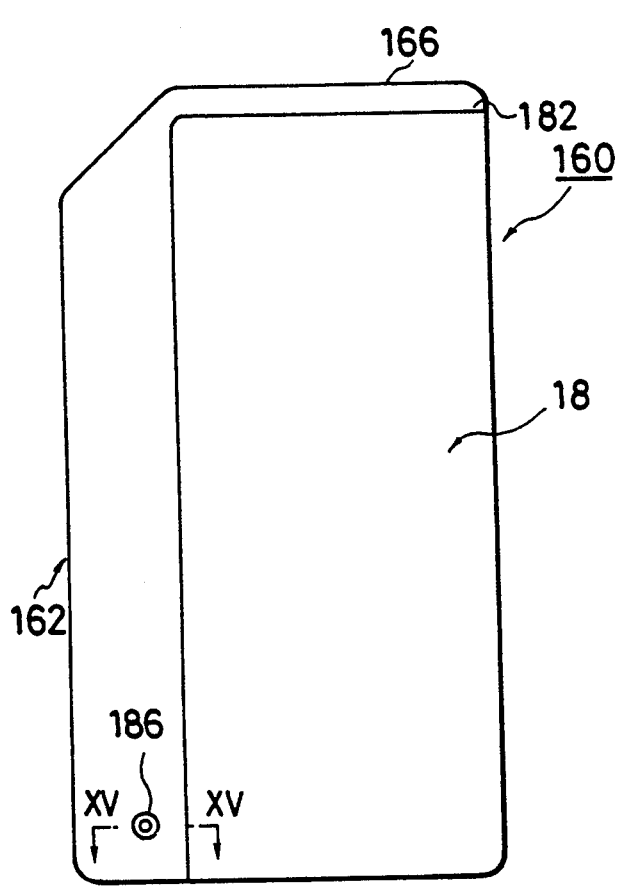
FIG. 13 is a side elevational view thereof.
Figure 14:
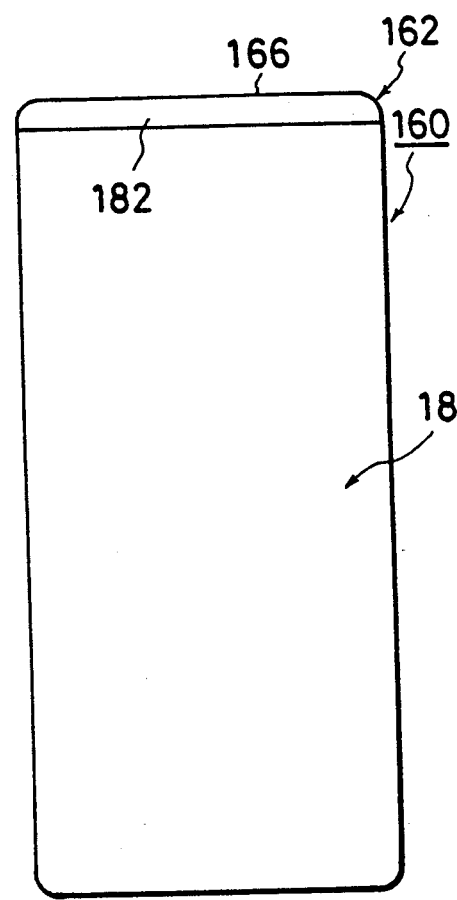
FIG. 14 is a front elevational view thereof.
Figure 15:
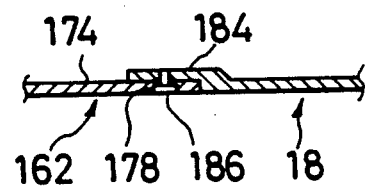
FIG. 15 is a fragmentary cross sectional view thereof.
Figure 16:
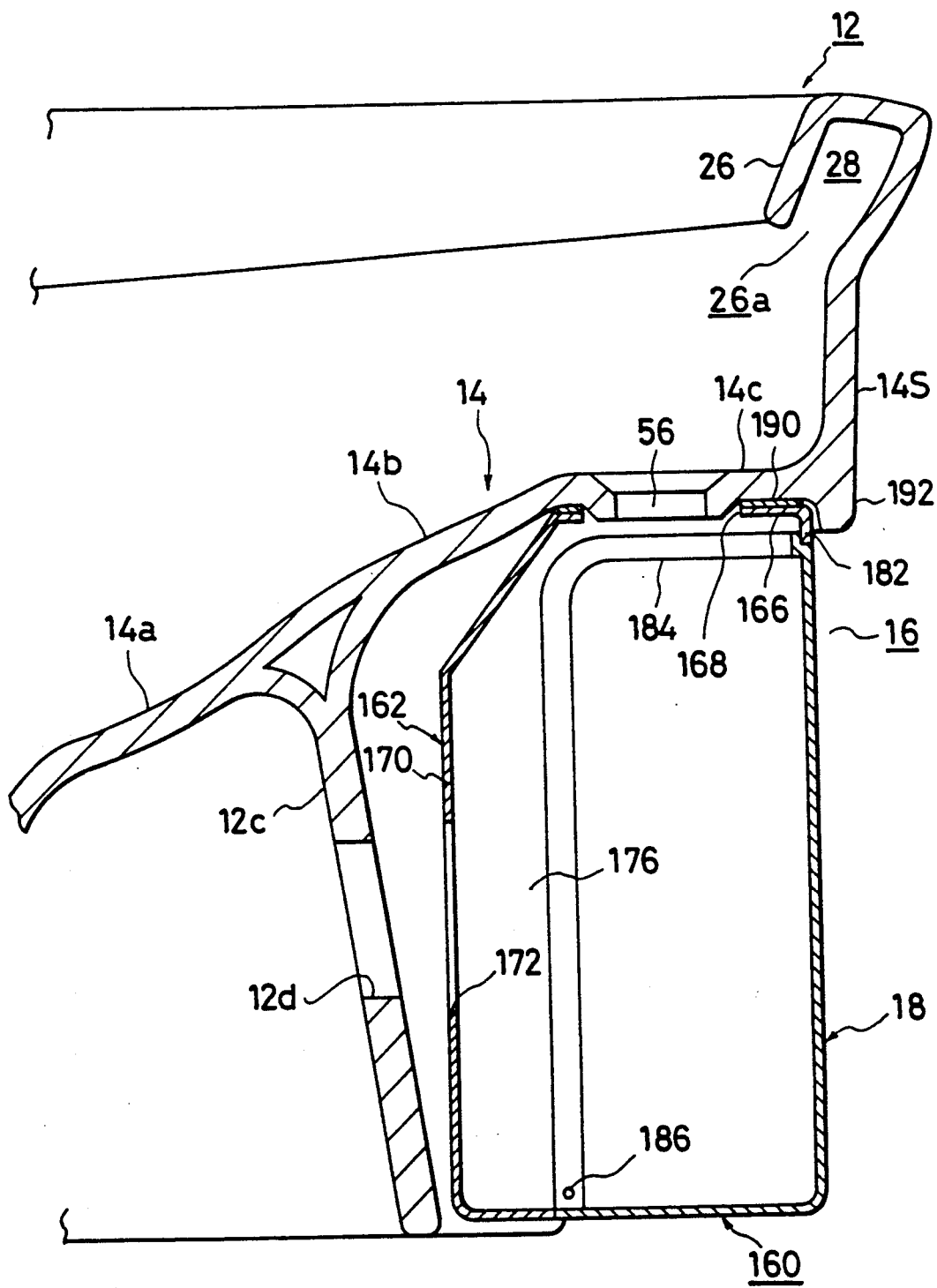
FIG. 16 is an explanatory view for the combination of a closure member and a toilet stool.

The structure of disposing the cover 18 is to be explained referring to FIGS. 10–16. FIG. 10 is a perspective view for assembling a closure member 160, FIGS. 11 through 14 are, respectively, plan view, rear elevational view, side elevational view and front elevational view of the closure member 160, FIG. 15 is a cross sectional view taken along line XV—XV in FIG. 13. FIG. 16 is a view showing the combination of the closure member 160 and the toilet stool 12, in which the urine detection device 20 is not illustrated in FIG. 16.

The closure member 160 comprises a box 162 and the cover 18. The box 162 has a recess 164 to which the cover 18 is engaged. When the cover 18 is mounted to the recess 164, the box-like closure member 160 is constituted. A circular opening 168 is formed to the upper surface 166 of the box 162 for inserting the urine sampling cylinder 50. An opening 172 is formed at the rear face of the box 162, through which the pipelines $L_1$, $L_3$, $L_7$, $L_8$ and electric wirings (not illustrated) are led out. The recesses 164 are formed on the sides 174 and 176 of the box 162 and small screw insertion holes 178 and 180 are perforated near the recess 164.

The box 162 has a curved portion 182 which is curved in an arcuate form so as to connect the side faces 174 and 178, and the curved portion 182 is in contiguous with an upper surface 166.

The cover 18 has a U-shaped curved portion corresponding to the curved portion 182. An insertion portion 184 is disposed at both sides and the upper edge of the cover 18 so as to be inserted into the rear face at the edge of the recess 164 of the box 162. Small screw insertion holes corresponding to the holes 178 and 180 are formed at the positions aligning with the insertion portion 184, so that when the insertion portion 184 is inserted on the rear side of the recess 164 and the small screw are inserted through the insertion holes 178, 180 and screwed into the insertion portion 184, the cover 18 and the cover box 162 are connected integrally.

As shown in FIG. 16, the box 162 is bonded at its upper surface 166 to the lower surface of the third bowl surface 14c of the bowl 14 by means of adhesive 190, etc. In this case, the box 162 is positioned and situated such that the circular opening 168 is in coaxial with the opening 56 and the recess 164 is directed to the front of the toilet stool 12. The box 162 is mounted to the bowl 14 before attaching the urine detection device 20 to the bowl 14.

As shown in FIG. 16, a suspending portion 192 is disposed to the upper edge for the opening 16 of the toilet stool 12 and the suspending portion 192 is disposed ahead of the box 162, so that it covers the upper portion of the box 162 (curved portion 182 in this embodiment). Therefore, water droplets falling along the outer circumferential surface 14S of the bowl 14 drop from the suspending portion 192, thereby preventing the droplets from going around the lower side of the third bowl surface 14c. Further, since the insertion portion 184 at the edge of the cover 18 is inserted to the rear face at the edge of the recess 164 of the box 162, if droplets falls from the suspending portion 192, it should be spread around the curved portion 182, and water does not intrude to the inside of the closure member 160.

Figure 17:
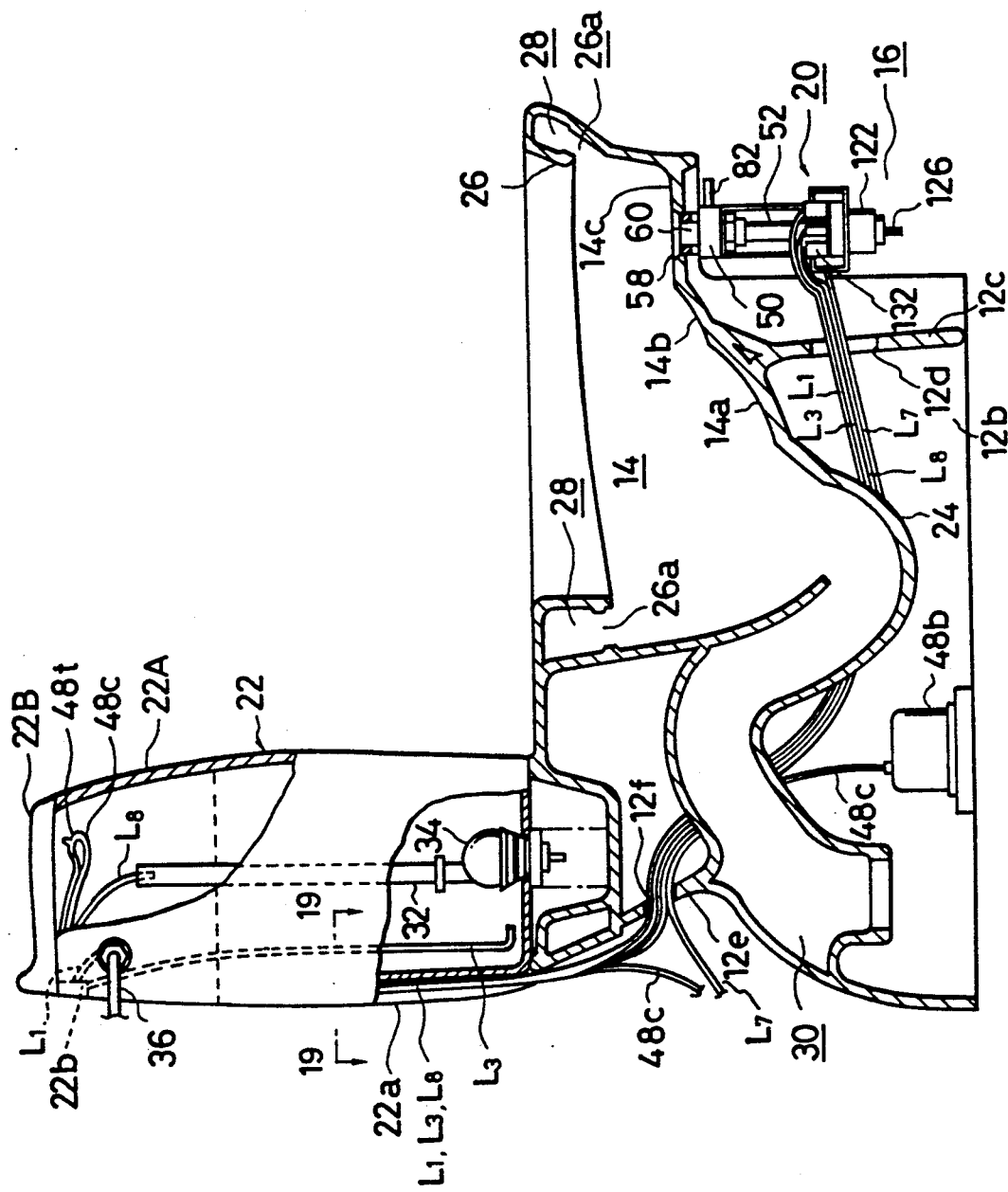
FIG. 17 is a cross sectional view of a toilet stool.
Figure 18:
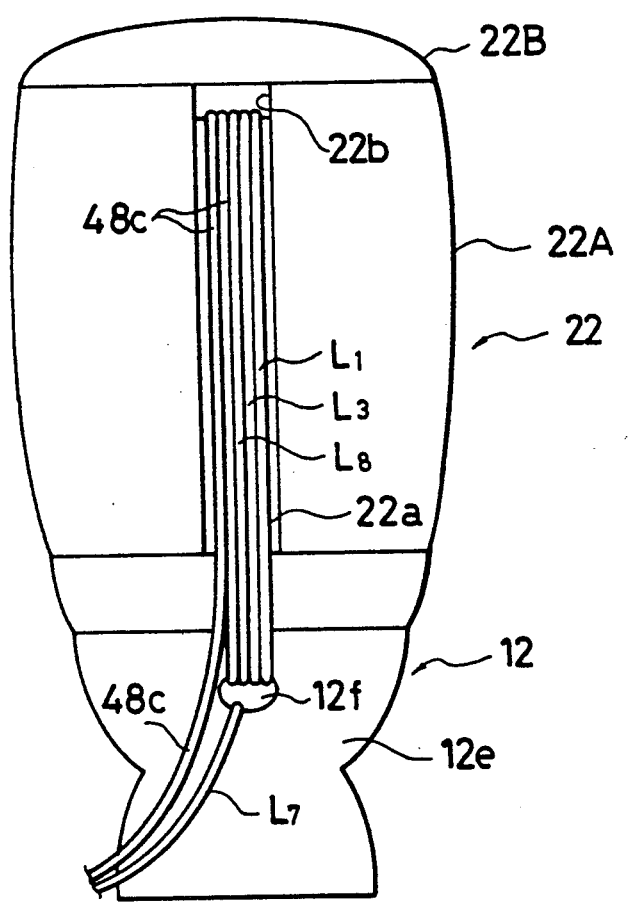
FIG. 18 is a rear elevational view of the toilet stool.
Figure 19:
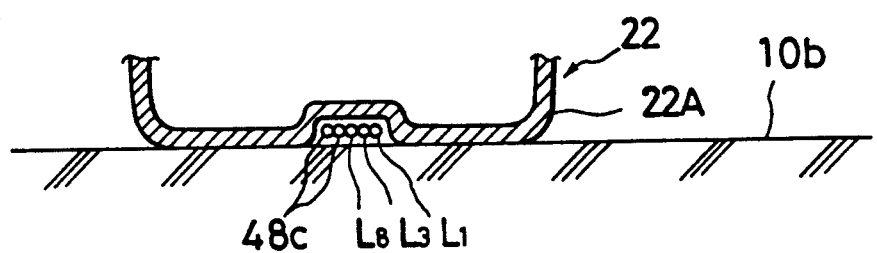
FIG. 19 is a fragmentary cross sectional view of a cistern taken along line XIX—XIX in FIG. 17.

FIGS. 17, 18 and 19 show another embodiment of the present invention.

In this embodiment, the cistern 22 comprises a main body 22A and a cover 22B. A recessed groove 22a extended vertically is formed at the rear face of the main body 22A. The recessed groove 22a is extended from a recess 22b formed at the upper end of the main body 22A to the vicinity of the lower portion of the main body 22A. As described later, pipelines $L_1$, $L_3$, $L_8$ led out from the peforation 12f of the toilet stool and an air pipeline 48c are extended through the recessed groove 22a and then introduced from the recess 22b to the inside of the cistern 22. Accordingly, the pipelines $L_1$, $L_3$, $L_8$ and the air pipeline 48c are not protruded from the rear face of the cistern 22 and the toilet stool can be disposed such that the cistern 22 is in close contact with the wall surface 10b of the toilet room 10.

The pipeline 48c is introduced through the recessed groove 22a and the recess 22b at the rear face of the cistern 22 into the cistern 22, passed through the portion of an opening 48t branched into a T-shaped form in the cistern 22 and then led out again from the recess 22b to the outside of the cistern 22. The pipeline 48c is further introduced through the recessed groove 22a and the perforation 12f into the toilet stool 12 and connected with the air pump 48b. By disposing the opening 48t, among a great amount of air sent from the air pump 48b, only the required amount of air is discharged through the opening 48t to the outside of the pipeline 48c and only an appropriate amount of air is supplied to the air diffuser pipe 48a. Further, when the operation of the air pump 48b is stopped and the pressure in the pipeline 48c tends to become negative, since atmospheric air flows from the opening 48t to the pipeline 48c, the reagent in the reagent reservoir 46 does not flow into the air pump 48b.

The pipelines $L_1$, $L_3$, $L_7$ and $L_8$ are led out together with the air pipeline 48c through the perforation 12f at the rear portion of the toilet stool 12. Among them, the pipelines $L_1$, $L_3$ and $L_8$, and the pipeline 48c are extended upwardly along the recessed groove 22a at the rear face of the cistern 22 and then introduced from the recess 22b to the inside of the cistern 22. As can be seen also in FIG. 2, the pipeline $L_3$ is disposed with the top end thereof reaching below the valve seat face of the ball valve 34, so that the residual water at the bottom of the cistern 22 can be supplied to the urine detection device 22 even if the ball valve 34 is opened to discharge water in the cistern 22 to the bowl 14. The pipeline $L_8$ is inserted to the inside of the overflow pipe 32. Water discharged from the top end of the pipeline $L_8$ flows by way of the inside of the overflow pipe 32 and the succeeding water passage to the inside of the ball 14. Those members carrying other reference numerals in FIGS. 17-19 are identical with the members of corresponding reference numerals explained previously.

Although the perforation 12f is opened at the rear face of the toilet stool 12 in the embodiment described above, the perforation 12f may be disposed to the rear end at the upper surface of the toilet stool 12.

The content of the control operation is to be explained.

When the preparatory switch 140 is pressed, the motor 96 of the stirring device 90 is driven, by which the stirring piece 78 starts rotation. Further, when the preparatory switch 140 is pressed, the preparatory operation for the urea detection as described below is effected, by which the urea detection device enters a stand-by state.

At first, flow channels for the 3-way valves 132-134 are selected such that communication for fluid flow is established between the pipeline $L_3$ and $L_4$, and $L_4$ and $L_5$. At the same time, the linear actuator 122 is rotated forwardly to rise the piston 54. This causes water in the urine sampling chamber C to overflow into the bowl 14 and water in the cistern 22 is introduced into the pump chamber P. After the piston 54 has reached the uppermost position the upper surface of the piston 54 slightly protrudes from the upper surface of the flange 58. The uppermost position is set, for example, by a limit switch (not illustrated), the rotation of the linear actuator 122 is reversed and the flow channel for the 3-way valves 132-136 are switched such that the communication is established only between the pipelines $L_5$ and $L_6$, and $L_6$ and $L_8$. Along with the start for the lowering of the piston 54, water in the pump chamber P is flown out by way of the pipelines $L_5$, $L_6$ and $L_8$ to the inside of the bowl 14. Water, etc. do not flow into the urine sampling chamber C, and the vacant volume in the urine sampling chamber C is increased along with the lowering of the piston 54. When the piston 54 is lowered to the lowermost position, the operation of the linear actuator 122 is stopped. This is the state where the stand-by state is completed and the inside of the urine sampling chamber C is made vacant except for slight residual water.

Then, a display indicating the discharge of urine is made on the display panel 144. When a person to be examined discharges urine, discharged urine splashes in the direction of the third bowl surface 14c of the bowl 14, flows into the urine sampling chamber C of the urine sampling cylinder 50 opened at the third bowl surface 14c and is then stored in the urine sampling chamber C.

After urine has been stored in the urine sampling chamber C, when the detection start switch 142 is pressed, the flow channels for the 3-way valves 132-136 are switched such that the communication is established only between the pipelines $L_3$ and $L_4$, and $L_4$ and $L_5$. Then, the linear actuator 122 rotates normally and the piston 54 starts rising.

In a case where the test start switch 142 is not depressed even after the elapse of 10 min from pressing the preparatory switch 140 described above, the linear actuator 122 is operated repeatedly to flush the urine detection device 20 as described later. When the detection start switch 142 is pressed within a predetermined time (within 12 min), the linear actuator 122 rotates normally to raise the piston 54 to the uppermost position. Thus, most of urine in the urine sampling chamber C overflows to the inside of the bowl 14, while leaving urine only in the clearance M between the piston 54 and the sampling cylinder 50. Water is introduced from the cistern 22 to the pump chamber P during raising of the piston 54.

Then, the flow channels for the 3-way valves 132–136 are selected such that communication is established only between the pipelines $L_2$ and $L_4$ and $L_4$, and $L_5$. At the same time, the linear actuator 122 is rotated reversely to lower the piston 54. Thus, water in the pump chamber P is introduced into the urine sampling chamber C to dilute urine. Since the stirring piece 78 is rotated in this instance, urine and water are mixed sufficiently.

Then, flow channels for the 3-way valves 132–136 are selected such that the communication is established only between the pipelines $L_5$ and $L_6$ and $L_6$ and $L_7$. At the same time, the linear actuator 122 is rotated forwardly to raise the piston 54. Thus, most of diluted unit in the urine sampling chamber C overflows into the bowl 14 and, at the same time, the reagent in the reagent reservoir 46 is introduced into the pump chamber P. When the piston 54 reaches the uppermost position, the reagent is filled in the pump chamber P and the diluted urine is present only in the clearance M in the urine sampling chamber C. From this state, the linear actuator 122 is rotated reversely and, at the same time, flow channels for the 3-way valves 132–136 are switched such that communication is established only between the pipelines $L_2$ and $L_4$, and $L_4$ and $L_5$. Along with the lowering of the piston 54, the reagent in the pump chamber P flows into the urine sampling chamber C, and the reagent is admixed with the diluted urine. In this case, the diluted urine and the reagent are rapidly and sufficiently mixed by the rotation of the stirring piece 78.

Figure 9:
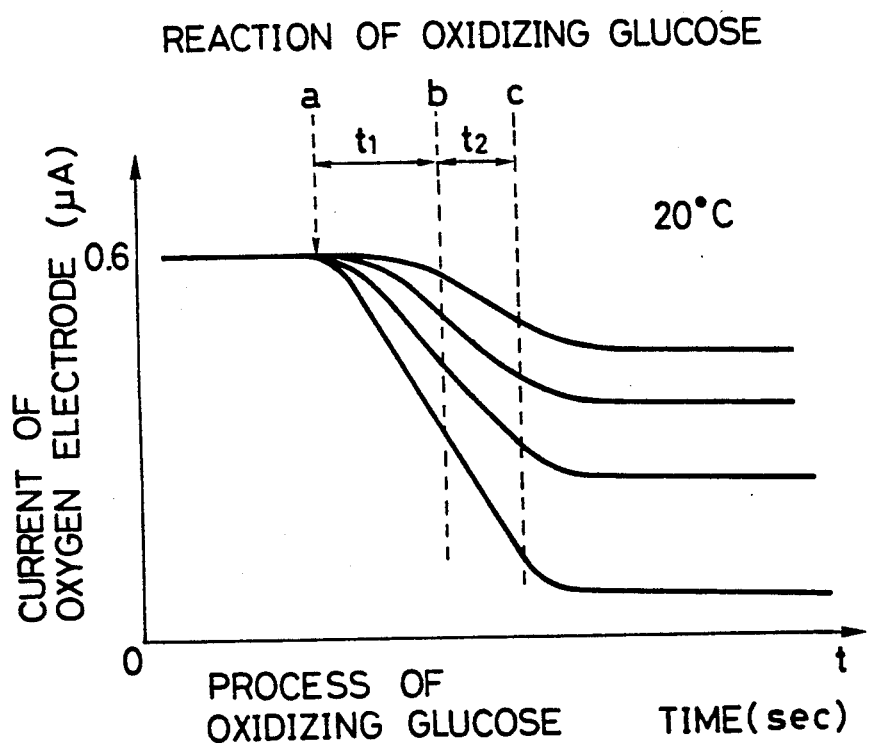
FIG. 9 is a graph showing the reaction of glucose.

Measurement with the oxygen electrode 82 is started when the piston 54 starts lowering and the reagent is started to be added to the diluted urine. The instance at which the mixing of the reagent, urine and diluting water is completed in the urine sampling chamber C is a time point a shown in FIG. 9. After this state, oxidizing reaction of glucose in urine proceeds to consume dissolved oxygen. Along with the reduction of the dissolved oxygen, resistance value between electrodes of the oxygen electrode 82 is increased and the current value is started to be lowered. As has been described above, since the oxygen is consumed at a higher rate as the content of the glucose in urine is increased, the current value from the oxygen electrode 82 is rapidly decreased. Accordingly, the concentration of glucose in urine can be detected by measuring the variation value of the current due to the oxygen electrode 82. Simultaneously, temperature in the urine sampling chamber C is measured by using the thermister 88, by which the detection value for the glucose concentration in urine is calibrated.

The detection signals from the oxygen electrode 82 and the thermister 88 are inputted to the control board in the control box 44 as described above, in which the concentration of glucose in urine is calculated, and the results are indicated on the display panel 144 for a predetermined period of time.

This embodiment employs a method of once discharging most of urine sampled in the urine sampling chamber C, conducting dilution with water, further discharging most of the diluted urine and mixing the remaining urine with the reagent. Further, the urine is stirred and mixed with the diluting water or the reagent by the stirring piece 78. Accordingly, a small amount of urine is efficiently brought into reaction with a great amount of reagent to efficiently oxidize glucose in urine.

In this embodiment, since air is blown into the reagent in the reagent reservoir 46, oxygen is dissolved into the reagent to a completely or substantially saturated level. Accordingly, the oxidizing reaction of glucose proceeds further efficiently and urine at high glucose concentration can also be measured at high accuracy.

In addition, in this embodiment, water in the cistern 22 containing sufficient amount of oxygen is used as the water for diluting urine in the urine sampling cylinder 50. That is, water in the cistern 22 is sprayed and discharged from the ball tap 38 to the inside of the cistern 22 and, since water is in a sufficient contact with air upon discharge (since water falls as fine droplets, area of contact between water and air is remarkably large). Accordingly, the dissolved oxygen in water in the cistern 22 is at a level of complete or substantial saturation. By using the water as the diluting water, glucose oxidation can be conducted more efficiently.

After the concentration of glucose in urine has been display on the display panel 144 for a predetermined period of time, the urine detection device 20 is flushed with a great amount of water till sufficient cleaning can be attained as described below. At first, the linear actuator 122 is rotated forwardly to raise the piston 54 and discharge the liquid mixture of reagent, urine and diluting water in the urine sampling chamber C to the inside of the bowl 14. In this instance, the 3-way valves 132–136 are so controlled that communication is established between the pipeline $L_3$ and $L_4$, and $L_4$ and $L_5$ to introduce water from the cistern 22 to the inside of the pump chamber P.

Then, flow channels for the 3-way valves 132–134 are selected so as to establish communication between the pipelines $L_2$ and $L_4$, $L_4$ and $L_5$ and, at the same time, 2-way valve 138 is opened. Simultaneously, the linear actuator 122 is rotated reversely to lower the piston 54 and water in the pump chamber P is introduced into the urine sampling chamber C. For this purpose, pipelines $L_2$–$L_5$ are at first flushed.

Then, the linear actuator 122 rotates forwardly to raise the piston 54, and water is introduced from the cistern 22 into the pump chamber P. Then, flow channels for the 3-way valves 134, 136 are selected so as to establish communication between the pipelines $L_5$ and $L_6$, and $L_6$ and $L_8$. Simultaneously, the linear actuator 122 is rotated reversely to lower the piston 54, and water in the pump chamber P is discharged to the overflow pipe 32. Thus, the pipelines $L_5$, $L_6$ are flushed.

Further, city water is introduced from the flushing nozzle 86 to the inside of the urine sampling cylinder 50 to flush the inside of the urine sampling cylinder 50 and the piston 54. Further, when the piston 54 lowers, city water jetted out from the flush nozzle 86 is directly spread to the oxygen electrode 82 to sufficiently flush the electrode 82. That is, city water maintained at a water supply pressure is introduced to the flushing nozzle 86 directly from the upstream to the valve portion of the ball tap 38 and the flushing nozzle 86 is disposed just opposed to the oxygen electrode 82. Accordingly, city water is vigorously jetted out toward the oxygen electrode 82 from the flushing nozzle 86, by which the oxygen electrode 82 is sufficiently flushed. Of course, water after colliding against the oxygen electrode flushes the inside of the urine sampling cylinder 50 or the surface of the piston 54. Further as has been described above, since the stirring piece 78 is rotated, flushing can also be conducted efficiently.

The process of jetting out water from the flushing nozzle 86 and vertically moving the piston 54 to introduce water into the pump chamber P is repeated till the detection value from the oxygen electrode 82 shows an output value in the case of flushing water. After the flushing has been conducted completely in this way, it is controlled such that the 2-way valve 138 is closed and communication between each of the pipelines $L_2$-$L_8$ for the 3-way valves 132-136 is interrupted, and the urine detection operation is completed.

In this embodiment, since the cover 18 is secured to the box 162 fixed to the toilet stool 12, the cover 18 can surely be secured. That is, the toilet stool 12 is usually made of porcelain with a low dimensional accuracy. Accordingly, if the cover 18 is directly attached to the toilet stool 12, securing failure may possibly be caused due to some or other reasons such as disalignment of small screw holes, etc. In this embodiment, the closure member can be made of metal or plastic and the closure member can be manufactured at a high dimensional accuracy. Accordingly, by previously attaching the box 162 to the toilet stool 12 (bowl 14), the cover 18 can be secured so as to be just fit the box 162.

In this embodiment, although the cover 18 is secured to the box 162 by means of small screws 186, other engaging means such as hooking fingers may also be used.

In this embodiment, although the opening 16 is disposed in front of the toilet stool 12, the opening 16 may be disposed on the side of the toilet stool 12.

In this embodiment, since the oxygen electrode 82 is attached to the urine sampling cylinder 50 such that it is situated on the side of the opening 16 of the toilet stool, the oxygen electrode 82 can easily be attached to or detached from the urine sampling cylinder 50 by inserting a hand through the opening 16. Accordingly, the oxygen electrode 82 can be exchanged or inspected rapidly and easily.

Further, in this embodiment, the urine sampling cylinder 20 is screwed with the sleeve 60 and the urine detection device 20 including the urine sampling cylinder 50 can be attached integrally to and detached from the toilet stool 12 by inserting a hand through the opening 16 and rotating the urine sampling cylinder 50.

In this embodiment, glucose oxidase is sealed in the reagent reservoir 46 to measure the concentration of glucose in urine. However, if bilirubin oxidase is sealed in the reagent reservoir, concentration of bilirubin in urine can be measured which is effective to the diagnosis of the healthy condition regarding liver disease. Furthermore, if a reagent containing lactate dehydrogenase as the main ingredient in the reagent reservoir, concentration of lactate in urine can preferably measured. Furthermore, if cholestrol oxidase is sealed in the reagent reservoir, concentration of cholesterol in urine can simply be determined. These reagents may be sealed in the reagent reservoir alone or as a mixture of such respective reagents. Further, if it is intended to provide a toilet stool having a function capable of simultaneously measuring bilirubin, lactate, cholesterol, etc. in addition to glucose in urine by using respective reagents individually, it is possible to dispose a plurality of independent urine detection devices 20 to a toilet stool by way of independent pipelines, thereby simultaneously measure the concentrations of glucose, bilirubin, lactate and cholesterol respectively from each of the urine detection device 20.

In this embodiment, since the urine sampling cylinder 50 is screwed to the sleeve 60, the urine sampling cylinder 50 can easily be attached to or detached from the toilet stool 12 by merely turning the urine sampling cylinder 50. Further, the linear actuator 122, the 3-way valves 132-136 and the 2-way valve 138 can also be attached or detached together with the urine sampling cylinder 50 or from to the toilet stool 12. Upon turning the urine sampling cylinder 50, it is preferred that the oxygen electrode 82 is previously removed from the urine sampling cylinder. Further, connection of the feed water pipelines or electric wirings to the urine sampling cylinder is also released.

In this way, since the cylinder can rapidly and easily attached to and detached from the bowl, assembling and repair can be made simply.

In this invention, an air diffuser pipe may be disposed in the cistern 22 for blowing air to the water in the cistern. For the air pump blowing air, the air pump 48$b$ for supplying air to the reagent reservoir 46 may be used in common. Further in the present invention, the cistern 22 may have a hand-washing pipe. When water falls from the top end of the water washing pipe into the cistern, oxygen in air dissolved into the water.

In the present invention, a strainer may be disposed to the pipeline $L_1$, so that obstacles do not flow into the urine sampling device 20.

Figure 20:
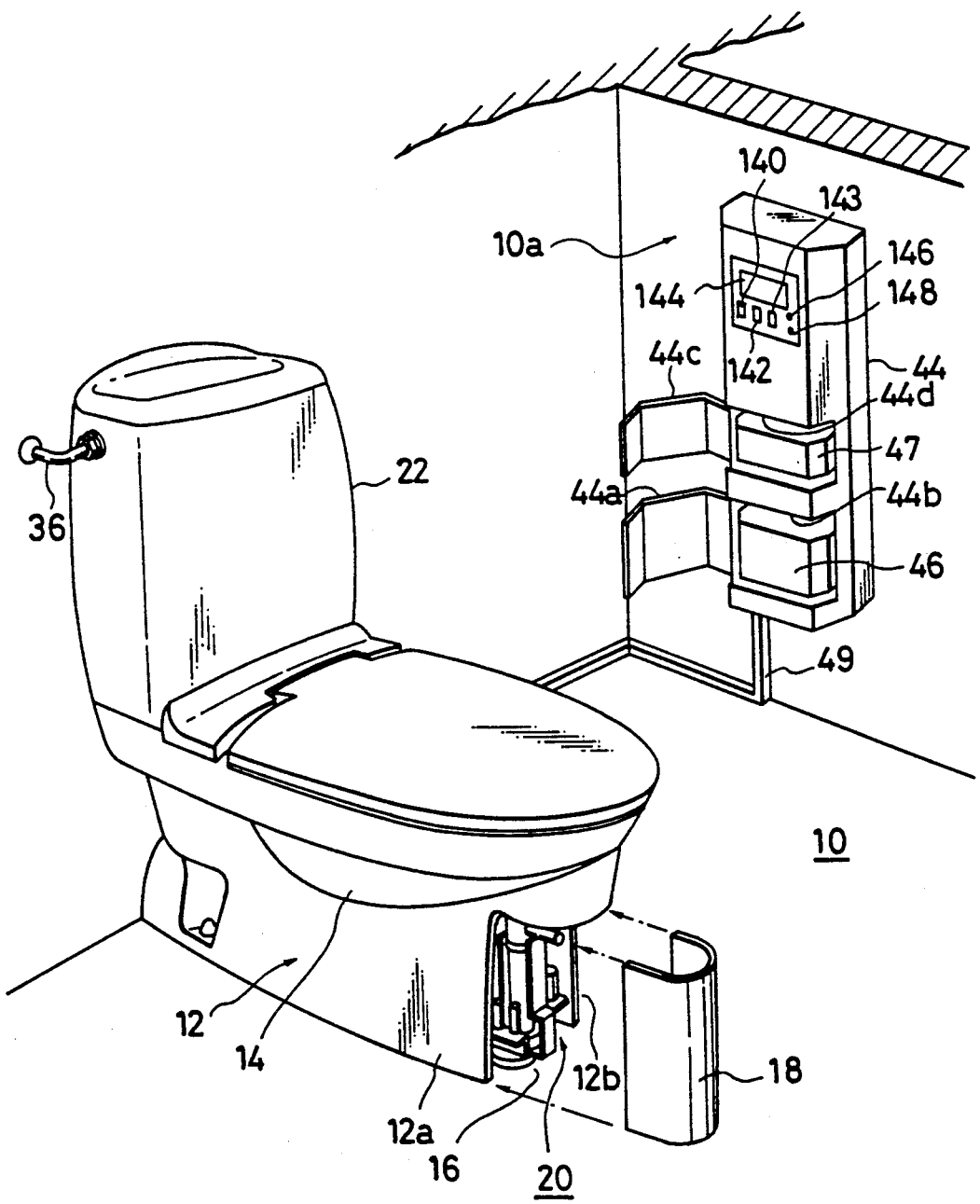
FIG. 20 is a perspective view of a toilet stool equipped with a detection device.
Figure 21:
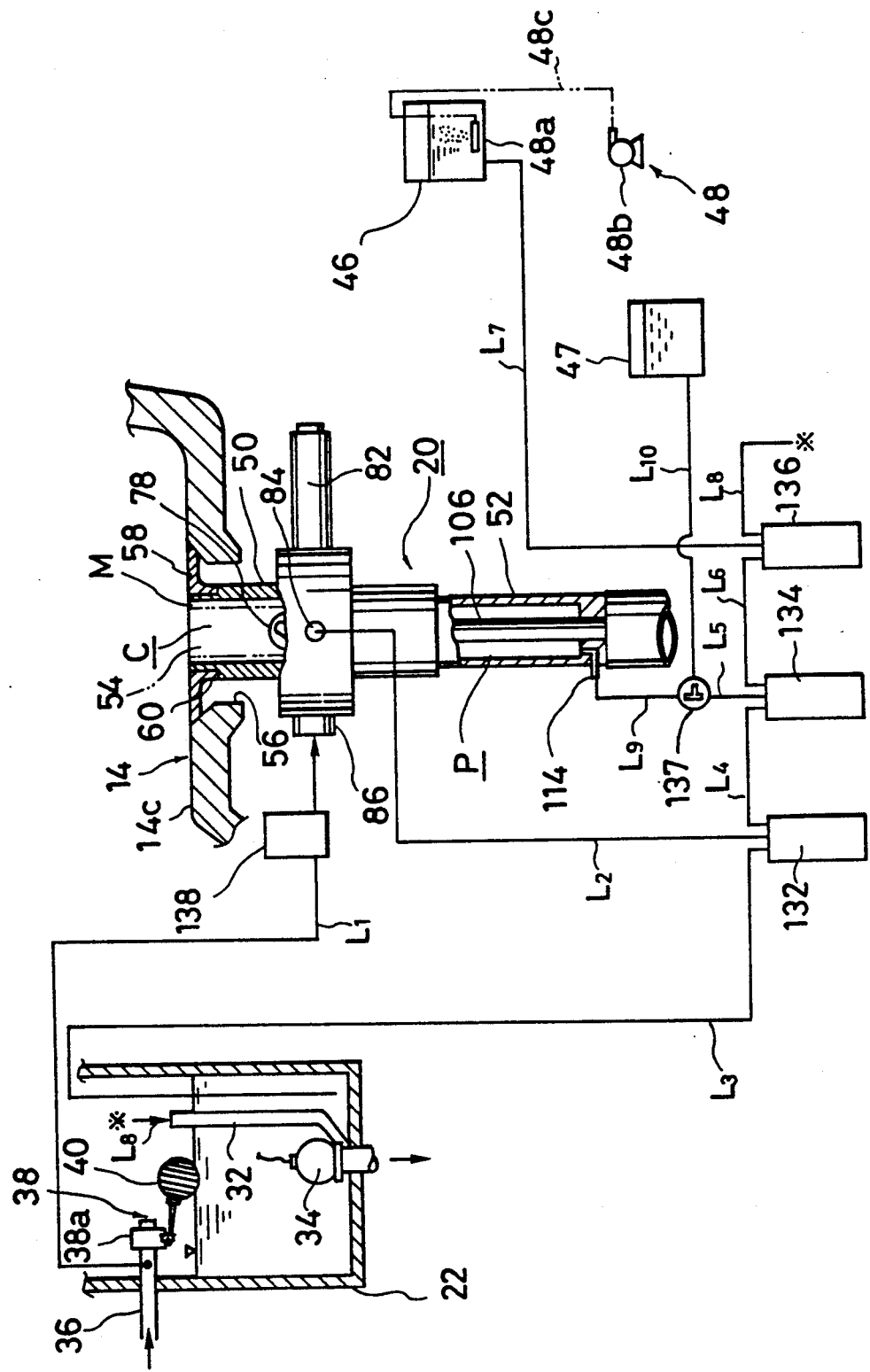
FIG. 21 is a diagram showing the pipeline systems.
Figure 22:
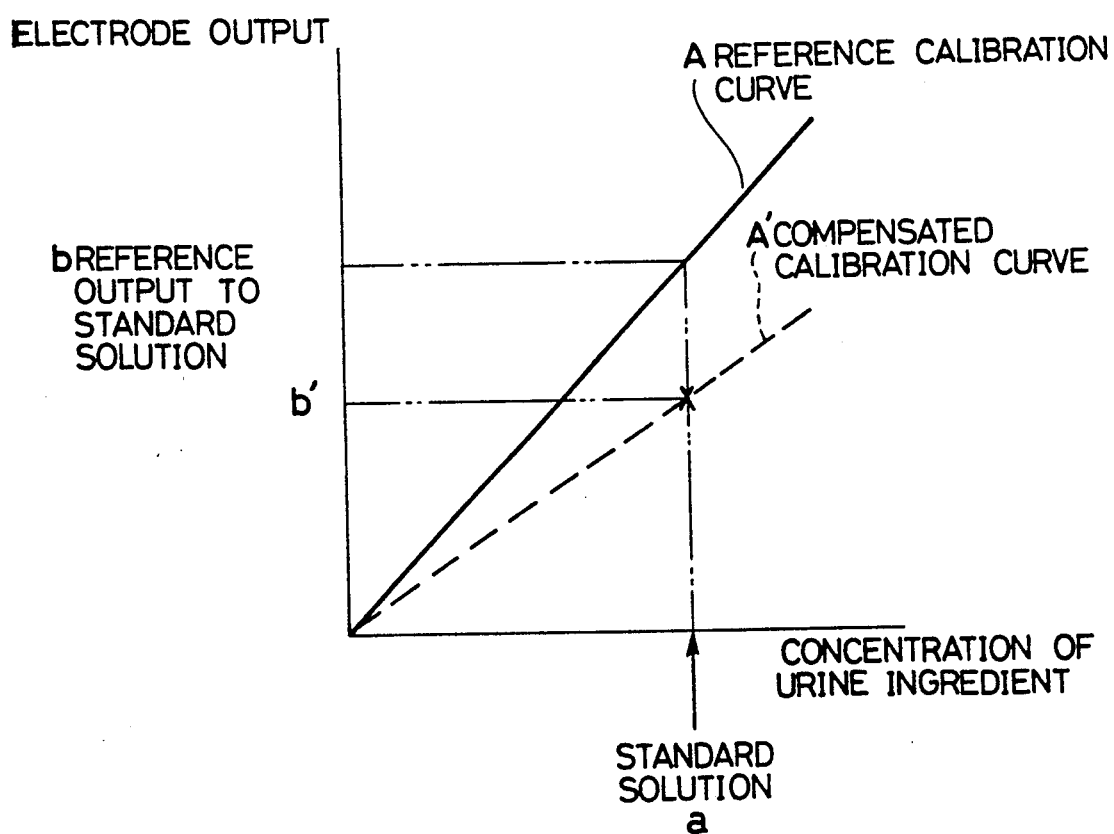
FIG. 22 is a graph showing calibration curves for the electrode output value and the urine ingredient.

Explanation is to be made for a further embodiment of the present invention referring to FIGS. 20 and 21.

As shown in FIG. 20, a control box 44 is disposed to the wall surface 10$a$ of a toilet room 10 and a reagent reservoir 46 and a standard solution reservoir 47 are disposed in the control box 44. The control box 44 also has an opening 44$b$ equipped with a door 44$a$ for exchanging the reagent reservoir 46 and an opening 44$d$ equipped with a door 44$c$ for exchanging the standard solution tank 47.

An air pipeline 48$c$, as well as a signal cable, a reagent pipeline and a standard solution pipeline are extended through the inside of the pipeline cover 49.

A support frame 116 is provided with four electrically driven 3-way valves 132, 134, 136 and 137 and a 2-way valve 138 by way of brackets 130 and 131. FIG. 21 is a diagram showing the pipeline connection for the 3-way valves 132-137, and the 2-way valve 138 with the urine sampling cylinder 50, the pump cylinder 52, the reagent reservoir 46, the bowl tap 38 and the cistern 22.

A flushing nozzle 86 of the urine sampling cylinder 50 is connected by way of a pipeline $L_1$ to a ball tap 38 at the upstream to a valve portion 38$a$.

The second port of the 3-way valve 134 is connected by way of a pipeline $L_5$ to the first port of the 3-way valve 137.

Water discharged from the top end of a pipeline $L_8$ is led out through the opening 12$f$ at the rear portion of the toilet stool 12.

In the 3-way valve 137, the second port is connected by way of a pipeline $L_{10}$ to a standard solution tank 47, while the third port is connected by way of a pipeline $L_9$ to the conduit hole 114 of the pump cylinder 52.

An electrode calibration switch 143 is disposed to the control box 44 and an aqueous glucose solution at a predetermined concentration is sealed in the standard solution reservoir 47. Other constituent members have been described previously for those members carrying the same reference numerals.

Then, the content of control is to be explained.

When the preparatory switch 140 is pressed, flow channels for the 3-way valve 137 is at first selected such that communication is made between the pipelines $L_5$ and $L_9$. The communicated state between the pipelines $L_5$ and $L_9$ is maintained unless the electrode calibration switch 148 is pressed.

Since the following control procedures are substantially the same as have been described above, only the difference is to be explained.

At the same time with the starting for the lowering of the piston 54, water in the pump chamber P is flown out by way of the pipelines $L_9$, $L_5$, $L_6$, $L_8$ to the inside of the bowl 14.

If the detection start switch 142 or the electrode calibration switch 143 is not pressed even after the elapse of 12 min from the pressing to the preparatory switch 140, the linear actuator 122 is operated repeatedly to flush the urine detection device 20.

For calibrating the output value from the electrode 82, the preparatory switch 140 is at first pressed. Thus, after the urine sampling device C, the pump chamber P and the pipelines $L_2$- $L_5$, and $L_9$ have been flushed sufficiently, a display indicating that urine is to be discharged is displayed on the display panel 44.

Then, the electrode calibration switch 143 is pressed. Then, after switching the 3-way valve 137 such that the communication is established between the pipelines $L_9$ and $L_{10}$, the linear actuator 122 is rotated forwardly and the standard solution is introduced from the standard solution reservoir 47 into the pump chamber P. After the piston 54 has reached to the uppermost position, flow channels for the 3-way valves 137, 134 and 132 are selected so that communication is established between the pipelines $L_9$ and $L_5$, $L_5$ and $L_4$, and $L_4$ and $L_2$ and, thereafter, the linear actuator 122 is rotated reversely. This causes the standard solution in the pump chamber P to introduce by way of the pipelines $L_9$, $L_5$, $L_4$ and $L_2$ to the inside of the urine sampling chamber C. Subsequently, after the standard solution is diluted in the same manner as in the urine detection process described above, the reagent is added and the electrode 82 is actuated to detect the glucose concentration. The detection value is inputted to the calculation circuit of the control board and stored as a compensation coefficient in the calculation circuit.

The calibration for the electrode is preferably conducted periodically, for example, once per day. Further, also upon replacing the electrode or the urine detection device, it is preferred to press the electrode calibration switch 143 after pressing the preparatory switch 140 prior to the urine detection. In this way, by calibrating the electrode output, urine detection can be conducted at an extremely high accuracy.

After the concentration of glucose urine has been indicated on the display panel 144 for a predetermined period of time or after the calibration of the electrode output value has been completed, the urine detection device 20 is flushed with a great amount of water till it is sufficiently cleaned in the same manner as described above.

A still further embodiment of the present invention is to be explained referring to FIGS. 23 through 26.

Figure 23:
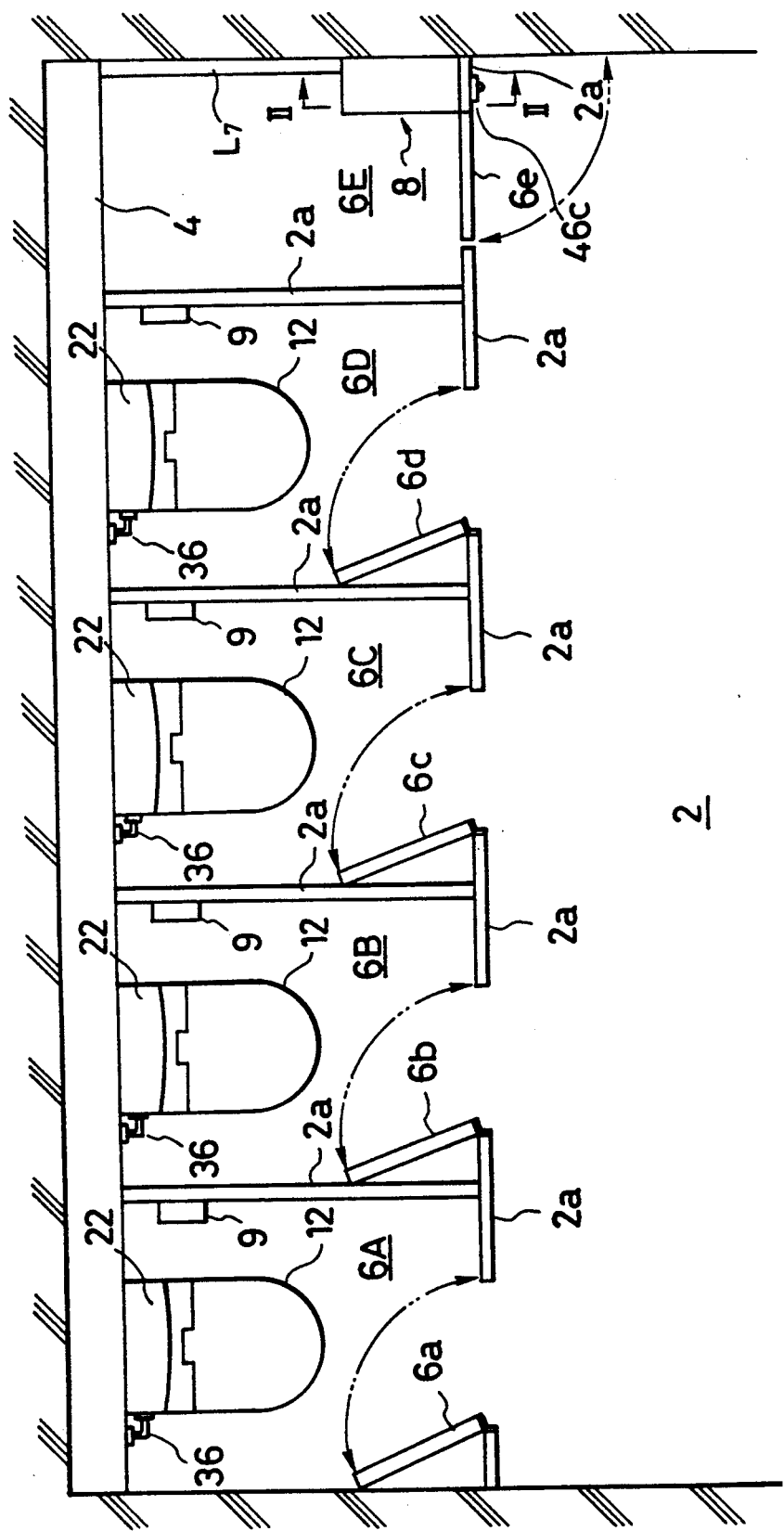
FIG. 23 is a top plan view of a system for urine detection facility according to one embodiment of the present invention.

In FIG. 23, a counter 4 is disposed in a room 2 for urine detection facility and small chambers 6A, 6B, 6C, 6D and 6E are disposed by being partitioned with partitioning panels 2a in front of the counter 4. Each of the small chambers 6A-6D is provided with control box 9 and a toilet stool 12 equipped with a urine detection device as described before. The small chamber 6E constitutes a chamber for containing cleaning tools or equipments, etc. and a reagent supply device 8 is disposed in thus small chamber 6E. Each of reference numerals 6a, 6b, 6c, 6d, 6e represents an access door to each of the small chambers 6A-6E. Water supply pipes or water draining pipes, etc. to the toilet stools 12 are disposed in the counter 4.

Figure 24:
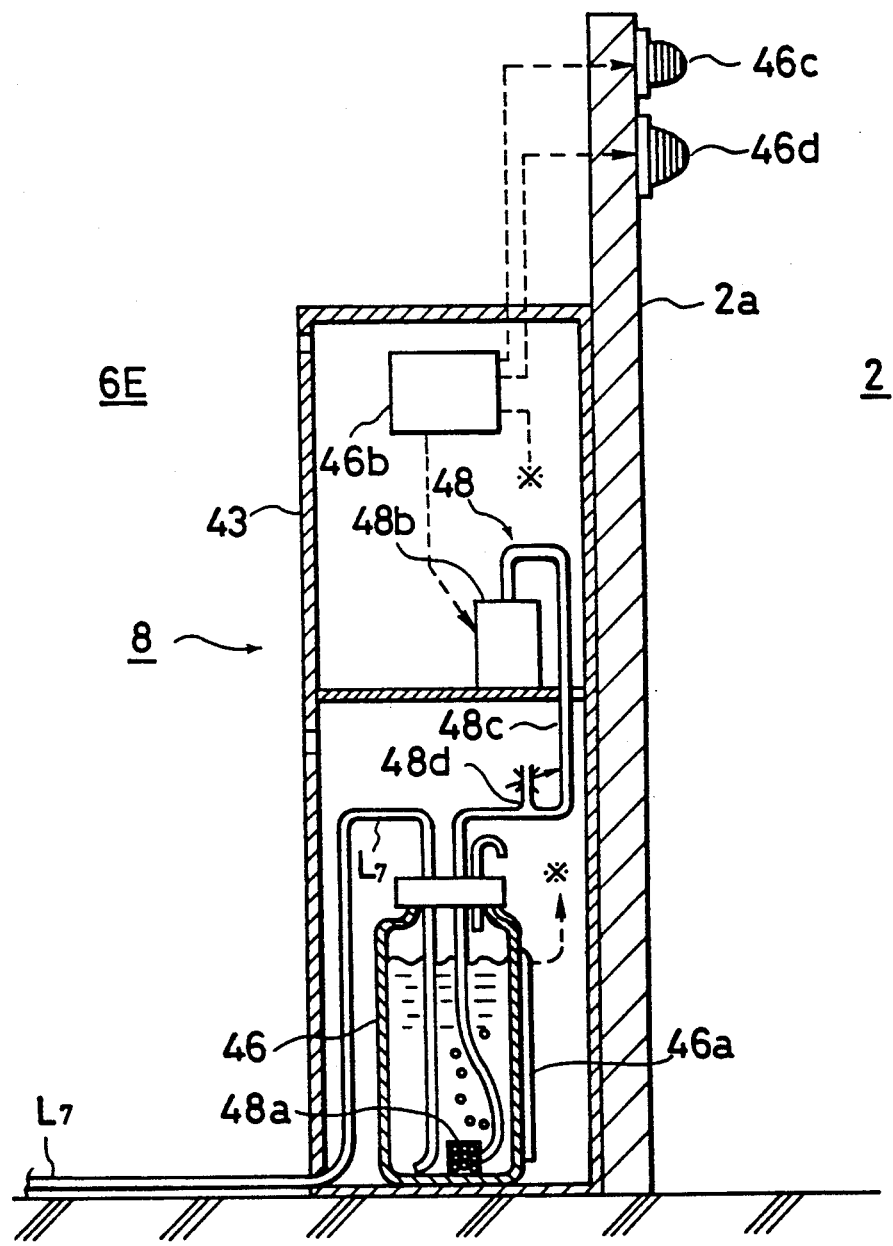
FIG. 24 is a cross sectional view taken along line XXIV—XXIV in FIG. 23.
Figure 25:
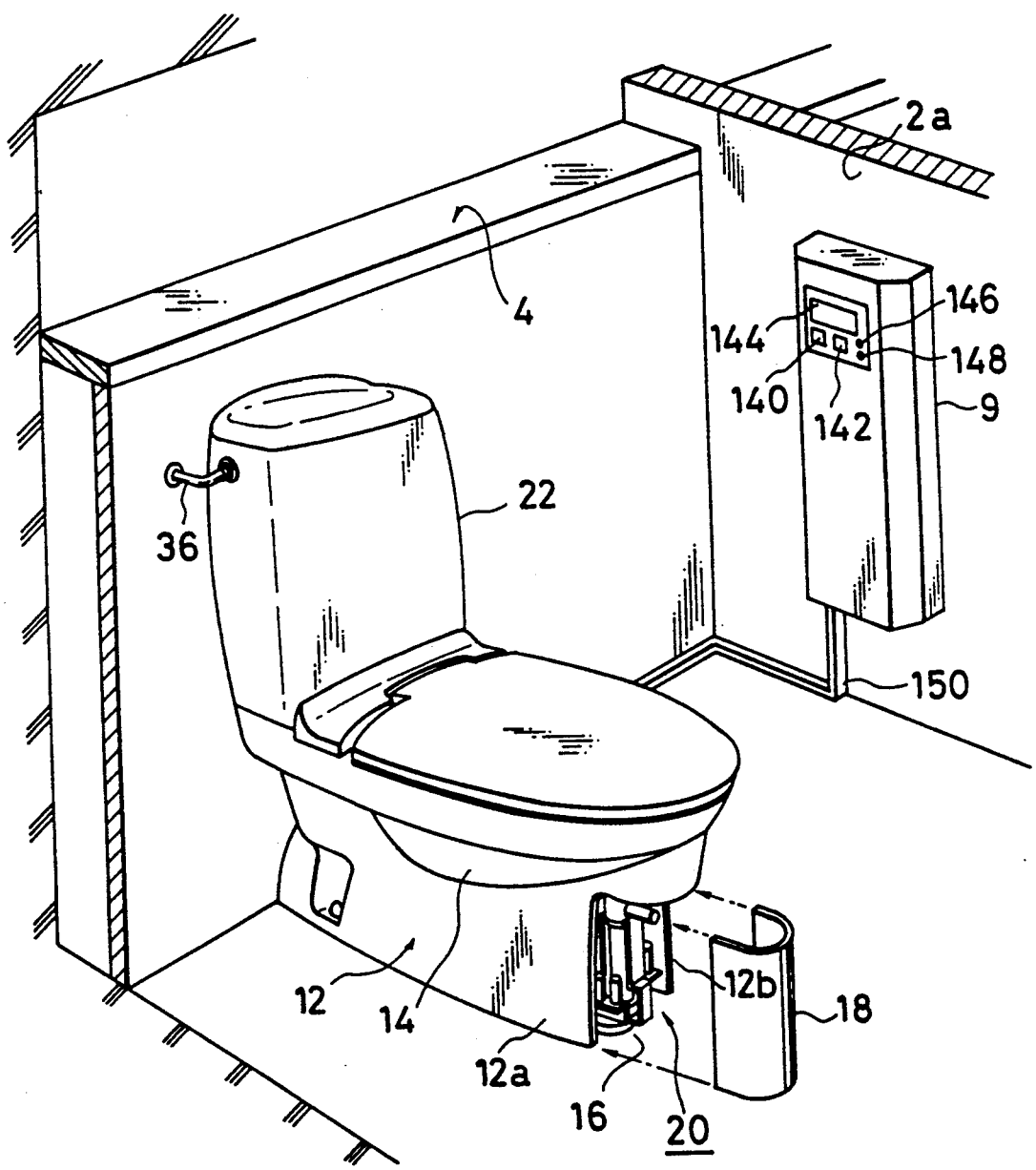
FIG. 25 is a perspective view of a toilet stool equipped with a urine detection device.
Figure 26:
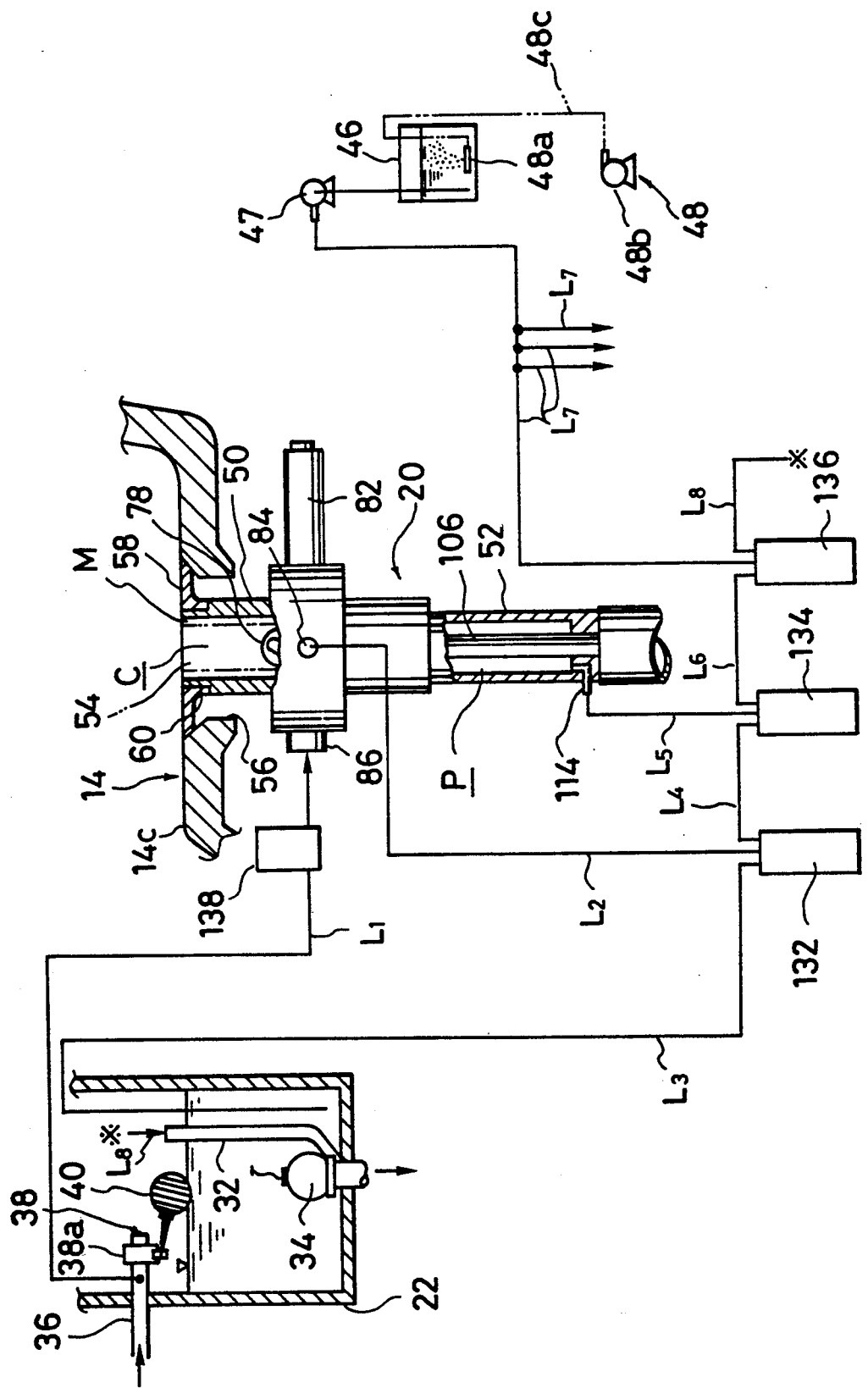
FIG. 26 is a diagram showing a pipeline system.

In FIGS. 23 and 24, reference numerals 43 denotes a casing, which is equipped with an opening/closing door (not illustrated) equipped with a lock at the front part thereof. A reagent reservoir 46 is disposed on the lower stage at the inside of the casing 43. A pipeline $L_7$ is connected to the reagent reservoir 46. The pipeline $L_7$ is connected through the inside of the counter 4 to the urine detection device 20 for each of the toilet stools 12 (refer to FIG. 26).

The reagent reservoir 46 is attached with a liquid level gage 46a and a detection signal is inputted to an electric circuit 46b. The electric circuit 46b turns on a green lamp 46c in a case when the liquid level in the reagent reservoir 46 is sufficiently high, while turns on a red lamp 46d in a case when the liquid level is lowered to less than a predetermined level. The electric circuit 46b is disposed with a driving circuit for air pump 48b.

In this embodiment, an opening 48d equipped with a variable restriction valve is disposed at the midway of a pipeline 48c.

In the embodiment as described above, since the reagent is supplied from the reagent reservoir 46 which is used in common with the urine detection devices 20 for the respective toilet stools 12, the reagent residue control may be effected only to one reagent reservoir 46, which facilitates the administration. Further, if there is no more reagent residue, only one reagent reservoir 46 may be replaced. Further, since green or red lamp 46c or 46d is turned on depending on the residue in the reagent reservoir 46, the reagent residue can be confirmed at a glance, which is convenient. In this embodiment, although only one reagent reservoir 46 is shown, a plurality of reservoirs may be disposed in parallel. In this case, reservoir for two or more kinds of reagents may be disposed in parallel.

In this embodiment, although four toilet stools 12 each equipped with urine detection device are disposed, they may be disposed by the number of 2, 3, 5 or more.

What is claimed is:

1. An apparatus for detecting an ingredient in urine comprising, cylinder means vertically disposed along its axial direction and having an upper end opening defining an inlet for urine, said cylinder means including a diametrically enlarged upper portion and a lower portion, said diametrically enlarged upper portion having an inside diameter larger than that of the lower portion;

piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the upper portion;

driving means for vertically moving said piston means between the upper and lower portions of said cylinder means;

an electrode extending through a wall of said cylinder means in said diametrically enlarged upper portion and having a forward end to contact with a liquid in said cylinder means for detecting concentration of an ingredient of the liquid in said cylinder means;

reagent supplying means having an opening extending to the upper portion of the cylinder means, a reagent reservoir, a pipeline and a pump located between the reagent reservoir and said opening, and a valve disposed in said pipeline so that a reagent is supplied into the cylinder means when said valve is opened;

water supplying means having an opening extending to the upper portion of said cylinder means, a water supplying source, a pipeline connected between the opening and the water supplying source and a valve disposed in said pipeline so that water is supplied into said cylinder means when said valve is opened; and stirring means attached to the diametrically enlarged upper portion of the cylinder means for stirring the liquid in the diametrically enlarged upper portion of the cylinder means.

2. An apparatus as defined in claim 1, wherein the stirring means comprises:
   a recess formed in the wall of the cylinder means;
   a stirring piece made of a magnetic member enhoused rotatably in said recess;
   a magnet disposed on an outside of said cylinder means so as to magnetically attract the stirring piece; and
   a motor for rotating said magnet, thereby rotating said stirring piece.

3. An apparatus as defined in claim 1, further comprising means for calculating an electrode detection value.

4. An apparatus as defined in claim 3, wherein said calculating means further includes means for indicating a result of the calculation.

5. An apparatus as defined in claim 4, wherein the electrode is an oxygen electrode for externally outputting a amount of oxygen consumed through a oxidizing reaction between a enzyme reagent and a ingredient in urine as an electric current value.

6. An apparatus as defined in claim 3, further comprising a control device for conducting following steps:
   lowering the piston means to its lowermost position so that urine can be received within the cylinder means;
   raising said piston means to its uppermost position, so that urine remains only in the space diametrically enlarged upper portion of said cylinder means and said piston means;
   actuating the reagent supplying means and the water supplying means so that predetermined amounts of water and reagent are supplied in the cylinder means and mixed with urine by opening the valve while lowering the piston means to its lowermost position;
   operating stirring means in said step; and
   calculating the concentration of the ingredient in urine based on a detection signal from the electrode and indicating results on display means.

7. An apparatus as defined in claim 1, wherein the reagent is an enzyme reagent capable of reacting with ingredient in urine and the electrode is such an electrode as capable of externally outputting a state of reaction between said enzyme reagent and said ingredient in urine as an electric signal.

8. An apparatus for detecting an ingredient in urine comprising,
   cylinder means vertically disposed along its axial direction and having an upper end opening defining an inlet for urine, said cylinder means including a diametrically enlarged upper portion and a lower portion, said diametrically enlarged upper portion having an inside diameter larger than that of the lower portion;
   piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion;
   driving means for vertically moving said piston means between the upper and lower portions of said cylinder means;
   an electrode extending through a wall of said cylinder means in said diametrically enlarged upper portion and having a forward end to contact with a liquid in said cylinder means for detecting concentration of an ingredient of the liquid in said cylinder means;
   reagent supplying means having an opening extending to the diametrically enlarged upper portion of the cylinder means, a reagent reservoir, a pipeline and a pump located between the reagent reservoir and said opening, and a valve disposed in said pipeline so that a reagent is supplied into the cylinder means when said valve is opened;
   water supplying means having an opening extending to the diametrically enlarged upper portion of said cylinder means, a water supplying source, a pipeline connected between the opening and the water supplying source and a valve disposed in said pipeline so that water is supplied into said cylinder means when said valve is opened; and
   means for blowing air into said reagent reservoir to thereby dissolve oxygen into the reagent in said reagent reservoir.

9. An apparatus for detecting an ingredient in urine comprising,
   cylinder means vertically disposed along its axial direction and having an upper end opening defining an inlet for urine, said cylinder means including a diametrically enlarged upper portion and a lower portion, said diametrically enlarged upper portion having an inside diameter larger than that of the lower portion;
   piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion;

driving means for vertically moving said piston means between the upper and lower portions of said cylinder means;

an electrode extending through a wall of said cylinder means in said diametrically enlarged upper portion and having a forward end to contact with a liquid in said cylinder means for detecting concentration of an ingredient of the liquid in said cylinder means;

reagent supplying means having an opening extending to the diametrically enlarged upper portion of the cylinder means, a reagent reservoir, a pipeline and a pump located between the reagent reservoir and said opening, and a valve disposed in said pipeline so that a reagent is supplied into the cylinder means when said valve is opened;

water supplying means having an opening extending to the diametrically enlarged upper portion of said cylinder means, a water supplying source, a pipeline connected between the opening and the water supplying source and a valve disposed in said pipeline so that water is supplied into said cylinder means when said valve is opened; and a flushing nozzle disposed in said cylinder means such that water jetted out therefrom is sprayed to the forward end of the electrode.

10. An apparatus as defined in claim 9, wherein the flushing nozzle is connected by way of a pipeline and a valve to a city water pipeline and water is jetted out from the flushing nozzle by the pressure of water in the city water pipeline.

11. A apparatus for detecting an ingredient in urine, comprising:

a toilet stool having a toilet bowl with a urine receiving surface;

cylinder means attached to the urine receiving surface of the bowl of the toilet stool and having a through hole, urine being supplied to the cylinder means through the through hole, said cylinder means being vertically disposed along its axial direction and having an upper end opening so that the upper end opening defines an inlet for urine, said cylinder means including a diametrically enlarged upper portion and a lower portion, said diametrically enlarged upper portion having an inside diameter larger than that of the lower portion;

piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion;

driving means for vertically moving said piston means between the upper and lower portions of said cylinder means;

reagent supplying means for adding a reagent to urine introduced into the diametrically enlarged upper portion of the cylinder means, an electrode attached to the diametrically enlarged upper portion of the cylinder means, said electrode contacting urine incorporated with the reagent for detecting ingredient in urine; and standard solution supplying means for supplying a standard solution for calibrating the electrode in the cylinder means.

12. An apparatus as defined in claim 11, further comprising water supplying means having an opening extending to the diametrically enlarged upper portion of said cylinder means, a water supplying source, a pipeline connected between the opening and the water supplying source and a valve disposed in said pipeline so that water is supplied into said cylinder means when said valve is opened.

13. An apparatus for detecting an ingredient in urine comprising, a toilet stool having a bowl with a urine receiving surface, said bowl having a through hole in the urine receiving surface;

cylinder means vertically disposed along its axial direction and having an upper end opening defining an inlet for urine, said cylinder means including a diametrically enlarged upper portion and a lower portion, said diametrically enlarged upper portion having an inside diameter larger than that of the lower portion;

piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion;

driving means for vertically moving said piston means between the upper and lower portions of said cylinder means;

an electrode extending through a wall of said cylinder means in said diametrically enlarged upper portion and having a forward end to contact with a liquid in said cylinder means for detecting concentration of an ingredient of the liquid in said cylinder means;

reagent supplying means having an opening extending to the diametrically enlarged upper portion of the cylinder means, a reagent reservoir, a pipeline and a pump located between the reagent reservoir and said opening, and a valve disposed in said pipeline so that a reagent is supplied into the cylinder means when said valve is opened; and a sleeve inserted into the through hole in the urine receiving surface of said bowl and secured to said toilet stool, said cylinder means being screwed into a lower end of said sleeve.

14. An apparatus as defined in claim 13, wherein the driving means is secured to the cylinder means and when the cylinder means is rotated for screwing into said sleeve, the driving means is also rotated together with said cylinder means.

15. An apparatus for detecting an ingredient in urine comprising, a toilet stool having a bowl with a urine receiving surface, said bowl having a through hole in the urine receiving surface;

a flushing cistern for supplying flushing water to said toilet stool;

cylinder means vertically disposed along its axial direction so that urine flows through the through hole of the toilet stool to inside thereof, said cylinder means having an upper end opening to define an inlet for urine, said cylinder means including a diametrically enlarged upper portion and a lower portion, said diametrically enlarged upper portion having an inside diameter larger than that of the lower portion;

piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion;

driving means for vertically moving said piston means between the upper and lower portions of said cylinder means;

an electrode extending through a wall of said cylinder means in said diametrically enlarged upper portion and having a forward end to contact with a liquid in said cylinder means for detecting concentration of an ingredient of the liquid in said cylinder means;

reagent supplying means having an opening extending to the diametrically enlarged upper portion of the cylinder means, a reagent reservoir, a pipeline and a pump located between the reagent reservoir and said opening, and a valve disposed in said pipeline so that a reagent is supplied into the cylinder means when said valve is opened, said reagent reservoir being disposed separately from said toilet stool; and water supplying means having an opening extending to the diametrically enlarged upper portion of said cylinder means, a pipeline for introducing water from the flushing cistern to the opening, and a valve disposed in the pipeline so that water is supplied from the flushing cistern into the cylinder means when the valve is opened.

16. An apparatus as defined in claim 15, further comprising a recessed groove extending vertically at a rear face of the flushing cistern and a pipeline for introducing water from said flushing cistern to the cylinder means disposed within said recessed groove.

17. A toilet stool equipped with a urine detection device comprising:

a toilet stool having a bowl at a front portion and a flushing cistern disposed at an upper rear portion, said flushing cistern having a recessed groove vertically formed at the rear portion thereof, said bowl having a through hole formed at an upper surface for urine discharge;

a urine detection device connected to the through hole such that urine is received, said urine detection device including a reagent reservoir and an electrode for detecting an ingredient in urine, said urine detection device further including;

cylinder means vertically disposed along its axial direction and having an upper end opening so that the upper end opening defines an inlet for urine, said cylinder means including a diametrically enlarged upper portion and a lower portion, said diametrically enlarged upper portion having an inside diameter larger than that of the lower portion, piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion, and driving means for vertically moving said piston means between the upper and lower portions of said cylinder means; and a pipeline disposed between said urine detection device and said flushing cistern, said pipeline supplying water from the cistern to the urine detection device, said pipeline extending from the rear portion of the stool through the recessed groove.

18. An apparatus for detecting an ingredient in urine comprising:

a toilet stool comprising a bowl having an outer surface and a urine receiving surface, a through hole formed at the urine receiving surface of the bowl, a supporting portion surrounding the outer surface of the bowl, an opening formed at a supporting wall portion and a closure member for closing the opening;

cylinder means vertically disposed along its axial direction and attached to the bowl, said cylinder means including an upper end opening defining an inlet for urine a diametrically enlarged upper portion and a lower portion, said diametrically enlarged upper portion having an inside diameter larger than that of the lower portion;

piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion;

driving means for vertically moving said piston means between the upper and lower portions of said cylinder means;

an electrode extending through a wall of said cylinder means in said diametrically enlarged upper portion and having a forward end to contact with a liquid in said cylinder means for detecting concentration of an ingredient of the liquid in said cylinder means, and a rear end directed to the opening in the supporting wall portion;

reagent supplying means having an opening extending to the diametrically enlarged upper portion of the cylinder means, a reagent reservoir, a pipeline and a pump located between the reagent reservoir and said opening, and a valve disposed in said pipeline so that a reagent is supplied into the cylinder means when said valve is opened; and water supplying means having an opening extending to the diametrically enlarged upper portion of said cylinder means, a water supplying source, a pipeline connected between the opening and the water supplying source and a valve disposed in said pipeline so that water is supplied into said cylinder means when said valve is opened.

19. An apparatus for detecting an ingredient in urine comprising:
- a toilet stool comprising a bowl having an outer surface and a urine receiving surface, a through hole formed at the urine receiving surface of the bowl, a supporting portion surrounding the outer surface of the bowl, an opening formed at a supporting wall portion and a closure member for closing the opening;
- a urine detecting device to which urine flows from the through hole, said opening in the supporting wall portion having a size to allow said urine detection device to pass therethrough, said urine detecting device comprising;
- cylinder means vertically disposed along its axial direction and having an upper end opening defining an inlet for urine, said cylinder means including a diametrically enlarged upper portion and a lower portion, said upper portion having an inside diameter larger than that of the lower portion;
- piston means fitted in said cylinder means, said piston means being movable between the upper and lower portions of the cylinder means, said piston means, when located in the lower portion, fitting in the lower portion without a space, and when located in the diametrically enlarged upper portion, said piston means forming a space between the piston means and the diametrically enlarged upper portion; and
- driving means for vertically moving said piston means between the upper and lower portions of said cylinder means.

* * * * *